(12) United States Patent
Jimenez et al.

(10) Patent No.: US 7,757,326 B2
(45) Date of Patent: Jul. 20, 2010

(54) TOOTHBRUSH WITH ENHANCED CLEANING EFFECTS

(75) Inventors: Eduardo Jimenez, Manalapan, NJ (US); John J. Gatzemeyer, Hillsborough, NJ (US); Thomas Mintel, Rahway, NJ (US)

(73) Assignee: Cologate-Palmolive Company, New York, NY (US)

( * ) Notice: Subject to any disclaimer, the term of this patent is extended or adjusted under 35 U.S.C. 154(b) by 0 days.

(21) Appl. No.: 10/697,213

(22) Filed: Oct. 30, 2003

(65) Prior Publication Data

US 2005/0091767 A1    May 5, 2005

(51) Int. Cl.
*A61C 17/22* (2006.01)
*A46B 9/04* (2006.01)

(52) U.S. Cl. ................... 15/22.1; 15/167.1

(58) Field of Classification Search .............. 15/21.1, 15/22.1, 22.2, 167.1, 172, 110
See application file for complete search history.

(56) References Cited

U.S. PATENT DOCUMENTS

| | | | |
|---|---|---|---|
| 1,770,195 A | 7/1930 | Burlew | 15/167.1 |
| 2,244,098 A | 6/1941 | Busick | 15/172 |
| 2,263,802 A | 11/1941 | Grusin | |
| 2,266,195 A * | 12/1941 | Lay Hallock | 15/167.1 |
| 2,706,825 A | 4/1955 | Blakeman | 15/176.4 |
| 3,129,449 A | 4/1964 | Cyzer | |
| 3,196,299 A | 7/1965 | Kott | |
| 3,316,576 A * | 5/1967 | Urbush | 15/22.1 |
| 3,398,421 A | 8/1968 | Rashbaum | |
| 4,114,222 A | 9/1978 | Serediuk | |
| 4,654,922 A | 4/1987 | Chen | |
| 4,694,844 A | 9/1987 | Berl et al. | |
| 4,783,869 A | 11/1988 | Lee | 15/22 |
| 5,305,492 A | 4/1994 | Giuliani et al. | |
| 5,325,560 A | 7/1994 | Pavone et al. | |
| 5,355,546 A | 10/1994 | Scheier et al. | 15/167.2 |
| 5,398,366 A | 3/1995 | Bradley | |
| 5,481,775 A | 1/1996 | Gentile et al. | 15/22.1 |
| 5,483,722 A | 1/1996 | Scheier et al. | 15/167.2 |
| 5,491,866 A | 2/1996 | Simonds | |
| 5,511,275 A | 4/1996 | Volpenhein et al. | |
| 5,524,319 A | 6/1996 | Avidor | |
| 5,528,786 A | 6/1996 | Porat et al. | 15/22.1 |
| 5,546,624 A * | 8/1996 | Bock | 15/22.1 |

(Continued)

FOREIGN PATENT DOCUMENTS

DE    19817704 A1    10/1999

(Continued)

OTHER PUBLICATIONS computer generated English translation of JP 2001-190333.*

*Primary Examiner*—Laura C Guidotti
(74) *Attorney, Agent, or Firm*—Amy M. Fernandez

(57) ABSTRACT

A toothbrush is provided for cleaning teeth with a mechanical vibratory element and a head having a plurality of different types of cleaning areas which provide for an enhanced cleaning effect upon vibration of said head by said mechanical vibratory element. The cleaning areas have different physical characteristics so that in addition to providing a varied cleaning effect from the cleaning areas themselves there is enhanced treatment as a result of the movement of the cleaning areas imparted by the mechanical vibratory device.

18 Claims, 16 Drawing Sheets

U.S. PATENT DOCUMENTS

| | | | |
|---|---|---|---|
| 5,625,916 A | 5/1997 | McDougall | |
| 5,628,082 A | 5/1997 | Moskovich | |
| 5,630,244 A | 5/1997 | Chang | |
| 5,651,158 A | 7/1997 | Halm | 15/167.1 |
| 5,689,850 A | 11/1997 | Shekalim | |
| 5,813,079 A | 9/1998 | Halm | |
| RE35,941 E * | 11/1998 | Stansbury, Jr. | 15/22.2 |
| 5,839,148 A * | 11/1998 | Volpenhein | 15/167.1 |
| 5,839,149 A | 11/1998 | Scheier et al. | 15/167.2 |
| 5,896,614 A * | 4/1999 | Flewitt | 15/167.1 |
| 5,946,759 A | 9/1999 | Cann | |
| 5,970,564 A | 10/1999 | Inns et al. | 15/201 |
| 5,987,688 A | 11/1999 | Roberts et al. | |
| 5,991,959 A | 11/1999 | Raven et al. | |
| 6,000,083 A | 12/1999 | Blaustein et al. | |
| 6,088,870 A | 7/2000 | Hohlbein | 15/167.1 |
| 6,141,817 A | 11/2000 | Dawson | 15/167.1 |
| 6,161,245 A | 12/2000 | Weihrauch | 15/201 |
| 6,178,582 B1 * | 1/2001 | Halm | 15/167.1 |
| 6,219,874 B1 | 4/2001 | van Gelder et al. | 15/167.1 |
| 6,276,021 B1 | 8/2001 | Hohlbein | |
| 6,311,358 B1 | 11/2001 | Soetewey et al. | |
| 6,311,360 B1 | 11/2001 | Lanvers | 15/191.1 |
| 6,338,176 B1 | 1/2002 | Smith et al. | 15/28 |
| 6,408,476 B1 | 6/2002 | Cann | 15/167.1 |
| 6,442,786 B2 * | 9/2002 | Halm et al. | 15/167.1 |
| 6,463,618 B1 * | 10/2002 | Zimmer | 15/110 |
| 6,553,604 B1 | 4/2003 | Braun et al. | |
| 6,564,416 B1 | 5/2003 | Claire et al. | |
| 6,641,764 B2 | 11/2003 | Lanvers | |
| 6,802,097 B2 * | 10/2004 | Hafliger et al. | 15/22.1 |
| 6,931,688 B2 | 8/2005 | Moskovich et al. | |
| 7,020,928 B2 * | 4/2006 | Hohlbein | 15/167.1 |
| 2002/0120991 A1 | 9/2002 | Cacka et al. | |
| 2002/0124333 A1 | 9/2002 | Hafliger | |
| 2003/0159224 A1 | 8/2003 | Fischer et al. | |
| 2003/0182744 A1 | 10/2003 | Fattori et al. | |
| 2004/0134007 A1 | 7/2004 | Davies | |
| 2004/0168269 A1 | 9/2004 | Kunita et al. | |
| 2004/0177462 A1 | 9/2004 | Brown, Jr. et al. | |
| 2004/0200016 A1 | 10/2004 | Chan et al. | |
| 2004/0255416 A1 | 12/2004 | Hohlbein | |

FOREIGN PATENT DOCUMENTS

| | | |
|---|---|---|
| EP | 0613636 A | 9/1994 |
| EP | 1350442 A | 10/2003 |
| FR | 38440 | 5/1930 |
| GB | 2371217 A | 7/2007 |
| JP | 401214306 A | 8/1989 |
| JP | 5-76416 A | 3/1993 |
| JP | 408322641 A | 12/1996 |
| JP | 2001190333 A | 7/2001 |
| JP | 2002-10832 | 1/2002 |
| WO | 2003037210 A | 5/2003 |
| WO | 2003043459 A | 5/2003 |
| WO | 2004/082428 | 9/2004 |

* cited by examiner

TOOTHBRUSH WITH ENHANCED CLEANING EFFECTS

FIELD OF THE INVENTION

The present invention relates to a toothbrush having a mechanical vibratory element and a head having different cleaning elements attached thereon. The present invention also relates to manually held and operated toothbrushes having flexibly mounted bristles. The present invention further relates to a toothbrush, either manual or powered, which includes a handle and a head having elements mounted to the head such as tufts of bristles and/or elastomeric wipers.

Documents cited in this text, and all documents cited or referenced in the documents cited in this text, are incorporated herein by reference. Documents incorporated by reference into this text or any teachings therein may be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

BACKGROUND OF THE INVENTION

A powered toothbrush is designed to assist a user by mechanically moving the head of the toothbrush. One approach in the art is to provide a vibratory element in the body of the toothbrush. U.S. Published Application No. 2002/0124333 relates to a mechanical vibratory device which causes the head part to vibrate. The vibratory device is accommodated in a front head part of the toothbrush, or in a neck-part region adjacent to the head part, said neck part connecting the head part to the handle, and is operatively connected to a power source, accommodated in the handle, via electrical connections running in the neck part, vibration-damping means preferably being provided in order to prevent vibration transmission to the handle, this achieves the situation where the vibrations which effect the improved cleaning action are produced predominantly in the head part and can only be felt to a slight extent in the handle, as a result of which comfortable handling of the toothbrush is achieved.

A number of approaches have been taken in the prior art to provide flexibility to the bristles during use of a toothbrush. U.S. Pat. No. 5,970,564, for example, discloses a toothbrush having an elastomeric ridge wherein there is a center array of bristles and there is a side array of bristles mounted in elastomeric boots. A number of patents disclose a toothbrush head having sets of bristles, each of which is mounted to a non-rigid or elastic support element. Examples of these approaches are found in U.S. Pat. Nos. 1,770,195, 2,244,098, 6,161,245 and 6,311,360 and in French Patent No. 38440.

The head of a conventional toothbrush usually has a flat or slightly altered surface to which cleaning elements are attached. Usually the cleaning elements are strands of plastic material(s) formed into tufts, bundles or other groupings. A goal of many toothbrushes is to accommodate the cleaning element profile to that of the teeth being cleaned. Achieving that goal is complicated by the difficulty in matching a toothbrush profile to the complex surface of a typical set of human teeth. The latter generally lie in a "C" shaped curve which presents the need for a brush to address a convex outer curve and a concave inner curve. In addition, the toothbrush should be capable of cleaning irregularities on the tooth surface as well as the interproximal area between teeth.

Blakeman U.S. Pat. No. 2,706,825 issued Apr. 26, 1955 discloses a replaceable bristle head for a toothbrush. The flexible head undulates in a manner so that rows of bristles move in a direction aligned with the axis of the toothbrush handle. U.S. Pat. Nos. 5,355,546, 5,483,722 and 5,839,149, all issued to Scheirer et al disclose cleaning elements mounted on a flexible membrane supported between a horseshoe shaped handle extension.

U.S. Pat. No. 5,651,158 issued Jul. 29, 1997 to Hans Halm discloses a toothbrush handle with a segmented head wherein adjoining segments are linked by an elastomeric material. The segments are primarily oriented transverse to the longitudinal axis of the toothbrush but may also be oriented parallel to that axis.

U.S. Pat. No. 6,088,870 discloses a latticework arrangement across the face of the toothbrush head. Tufts of cleaning elements are situated between the boundaries of the lattice and are mounted in the head so that each tuft flexes such that during brushing the bristle tufts will deflect in a manner that increases cleaning of the tooth surface.

U.S. Pat. No. 6,219,874 B1 issued Apr. 24, 2001 to Gelder, et al. discloses flexible mounting of toothbrush cleaning elements accomplished by segmenting portions of the toothbrush head, which segments are connected by flexible hinges.

U.S. Pat. No. 6,408,476 discloses another form of segmented toothbrush head with transverse grooves and an elastomeric portion joining the segments. A method of manufacturing this head is also disclosed.

It is well known that the ideal brushing technique from a dental hygiene perspective is an up and down stroke along the vertical surface of teeth which massages the gums while cleaning the teeth. However, due to a number of factors, including ergonomic difficulties, haste, lack of education or the like, few consumers use the recommended brushing technique. Rather, the typical consumer brushes across their teeth in a horizontal motion rather than a vertical movement. Various approaches have been taken by others to translate horizontal brush movement into partial vertical movement of the bristles or cleaning elements.

Translation of horizontal to vertical movement of cleaning elements is accomplished in U.S. Pat. No. 4,783,869 through use of a helix groove in a movable shaft within a toothbrush handle. The groove receives a pin which rides in the groove. This mechanism causes the toothbrush head to partially rotate or oscillate as the handle moves left-to-right or vice versa in the user's mouth. That rotation or oscillation causes the cleaning elements to move in a vertical plane perpendicular to movement of the toothbrush handle.

U.S. Pat. No. 5,481,775 discloses an arcuate shaped base for a toothbrush head aligned with the longitudinal axis of the head. A movable arcuate block containing cleaning elements is flexibly mounted on the toothbrush head. The block is free to slide on the head in a manner whereby the cleaning elements may travel in a vertical direction generally transverse to the typical side-to-side motion of the toothbrush.

U.S. Pat. No. 5,528,786 discloses pivotal mounting of cleaning elements that allows those elements to move up and down in concert with a side-to-side stroke along the teeth.

A general disclosure of flexible mounting for cleaning elements on a toothbrush head is contained in U.S. Pat. No. 5,839,149. In this patent the cleaning elements are mounted on a flexible membrane supported between a horseshoe shaped handle extension.

U.S. Pat. No. 6,141,817 discloses cleaning elements mounted on a flexible membrane that splay outward when the toothbrush is pressed against the user's teeth.

U.S. Pat. No. 6,338,176 B1 issued Jan. 15, 2002 to Smith, et al. discloses round sections of cleaning bristles mounted on individual pads that rotate within a toothbrush body. This converts backward and forward motion of the toothbrush into circular motion of the cleaning elements. The bristles associated with each pad are of varying height to accommodate irregularities, gaps, pockets and contours in natural tooth formation. The rotating cleaning elements can be supplemented with fixed cleaning elements adjacent thereto.

A toothbrush head should provide both proper support for the bristles, and be flexible enough during use to allow the bristles to conform to the shape of a user's mouth or teeth. Additionally, construction techniques should be inexpensive, versatile and consistent.

In an attempt to meet these criteria, a process known as "Anchor Free Tufting" ("AFT") has been used in the formation of toothbrush heads. In such an AFT process, a head plate for holding toothbrush bristles, and for eventual insertion into a toothbrush body, is typically formed of a rigid plastic that is conducive to sonic welding. The head plate is formed with a solid perimeter and defines a field of variously shaped and sized holes within this perimeter. Fibers that are to form the tufts are then placed in the holes in the field of the head plate, and the backs of the tufts are melted together to fix their position relative to one another.

The tufted head plate is then inserted into a predefined receiving portion of the head portion of a toothbrush handle and is sonically welded into place. The brush is then end-rounded and packaged for sale as a traditional toothbrush.

However, this manufacturing process results in a toothbrush with a very rigid head that does not easily conform to the physical characteristics of a user when brushing. Therefore, it would be desirable to provide a toothbrush that can be conveniently manufactured by the above process, but provides the desired flexibility of the head of the toothbrush during use.

It would also be desirable if a toothbrush could be provided having various cleaning elements on a head, such as bristles with different degrees of flexible mounting, to have a enhanced cleaning effect when moved by a mechanical vibratory element.

OBJECTS AND SUMMARY OF THE INVENTION

An object of this invention is to provide a toothbrush with a mechanical vibratory element and a head having a plurality of different types of cleaning areas which provide for an enhanced cleaning effect.

Another object of this invention is to provide a toothbrush having the head separated into different cleaning areas which differ from each other in the flexible mounting of the cleaning elements.

A further object of this invention is to provide such a toothbrush wherein some of the cleaning areas have the cleaning elements mounted on a relatively fixed or non-movable base while other cleaning areas are mounted on a flexible or elastic pod.

A still further object of this invention is to provide techniques for improving the manufacturability of toothbrushes such as indicated above or toothbrushes having only flexibly mounted cleaning elements.

In accordance with one embodiment of the invention, a toothbrush is provided having a handle; a head connected to said handle by a neck element; and a mechanical vibratory device which causes the head to vibrate, said mechanical vibratory device located in the head or in a region adjacent to the head and operatively connected to an electric power source, wherein said head comprises movable elements attached thereto for providing a enhanced cleaning effect upon vibration of said head by said mechanical vibratory element.

In accordance with another embodiment of the invention, a toothbrush is provided having a handle; a head connected to said handle by a neck element; and a mechanical vibratory device which causes the head to vibrate, said mechanical vibratory device located in the head or in a region adjacent to the head and operatively connected to an electric power source, wherein said head comprises a body portion and a plurality of separate cleaning areas, at least one of said cleaning areas comprising a base with at least one outwardly extending cleaning element, at least one of said cleaning areas being a pod having at least one outwardly extending cleaning element, said pod having a greater degree of movability than said base, and said pod being resilient whereby said at least one cleaning element of said pod is movable from an initial position and being returnable to said initial position.

In accordance with a further embodiment of the present invention, a method of forming a toothbrush is provided having a handle; a head connected to said handle by a neck element; and a mechanical vibratory device which causes the head to vibrate, said mechanical vibratory device located in the head or in a region adjacent to the head and operatively connected to an electric power source, wherein said head comprises a rigid body portion, a plurality of spaced pods extending outwardly from said body portion, each of said pods including a narrow resilient stem capable of moving from an initial position and being returnable to said initial position, a plate mounted to and across each of said stems, a plurality of cleaning elements mounted to and extending outwardly from each of said plates, and said stems being connected to each other by a support secured to said body portion.

In accordance with still another embodiment of the present invention, a method of forming a toothbrush is provided having a handle; a cleaning head connected to said handle by a neck element; and a mechanical vibratory device which causes the head to vibrate, said mechanical vibratory device located in the head or in a region adjacent to the head and operatively connected to an electric power source, comprising the steps of forming a unitary subassembly by molding a plurality of spaced pods wherein each of the pods has a thin elastic stem and an outwardly extending plate with a plurality of bristles extending outwardly from the plate and secured to the plate by an IMT procedure and wherein the spaced pods are interconnected to each other by a support integral with each of the stems to create the subassembly, providing a second subassembly from the handle and a portion of the cleaning head, and securing the unitary subassembly to the portion of the cleaning head to complete the cleaning head structure by the mounting of the unitary subassembly to the portion of the cleaning head.

In accordance with a still further embodiment of the present invention, a toothbrush is provided having a handle; a head connected to said handle by a neck element; and a mechanical vibratory device which causes the head to vibrate, said mechanical vibratory device located in the head or in a region adjacent to the head and operatively connected to an electric power source, wherein said head comprises a movable portion and a fixed portion surrounding the movable portion, cleaning elements mounted in the fixed and movable portions, a resilient membrane extending between at least a portion of the area between the fixed and movable portions and the membrane being capable of flexing to alter its original orientation during use of said toothbrush and then recovering to assume its original orientation randomly during use of said toothbrush.

In accordance with yet another embodiment of the present invention, a toothbrush is provided having a handle; a head connected to said handle by a neck element; and a mechanical vibratory device which causes the head to vibrate, said mechanical vibratory device located in the head or in a region adjacent to the head and operatively connected to an electric power source, wherein said head is flexibly mounted to the handle, the head having an upper face with fingers flexibly mounted, thereon, and ribs connecting the fingers to the upper face whereby flexure of the head or its upper face causes lateral movement of the fingers relative to the longitudinal axis of the toothbrush.

In accordance with a further embodiment of the present invention, a toothbrush is provided having a handle; a head connected to said handle by a neck element, said head comprising an outer perimeter portion formed of a rigid material, said rigid material being adapted to allow said head to be sonically welded; a tuft field positioned within said outer perimeter portion and being formed of a flexible elastomer, said tuft field defining one or more apertures to receive one or more bristle tufts, said head being sonically welded into place in said toothbrush; and a mechanical vibratory device which causes the head to vibrate, said mechanical vibratory device located in the head or in a region adjacent to the head and operatively connected to an electric power source.

In accordance with a another embodiment of the present invention, a method for forming a head for use with the toothbrush is provided by forming an outer perimeter portion of a rigid material, said rigid material being adapted to allow said head to be sonically welded; and positioning a tuft field within said outer perimeter portion, said tuft field being formed of a flexible elastomer, said tuft field defining one or more apertures to receive one or more bristle tufts; placing a bristle tuft within at least one corresponding aperture in said tuft field; melting a portion of bristles in said bristle tuft to secure said bristle tuft in said aperture in said tuft field; and sonically welding said tuft field into place in said toothbrush.

BRIEF DESCRIPTION OF THE DRAWINGS

In this specification and the accompanying drawings, some preferred embodiments of the invention are shown and described, and various alternatives and modifications thereof have been suggested. It is to be understood that these are not intended to be exhaustive and that many other changes and modifications can be made within the scope of the invention.

The suggestions herein are selected and included for purposes of illustration in order that others skilled in the art will more fully understand the invention and the principles thereof and will thus be enabled to modify it in a variety of forms, each as may be best suited to the conditions of a particular use.

Figure 1:
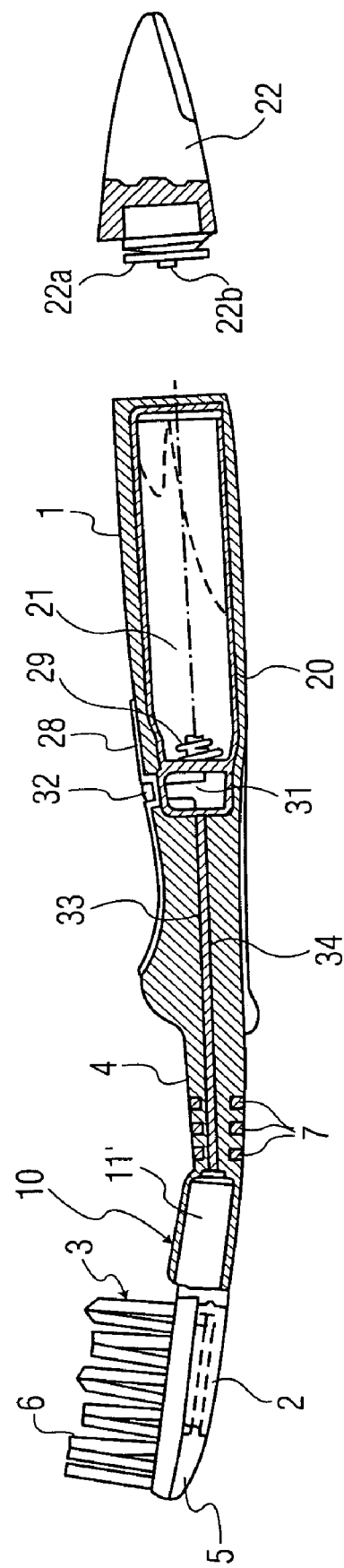
Figure 2:
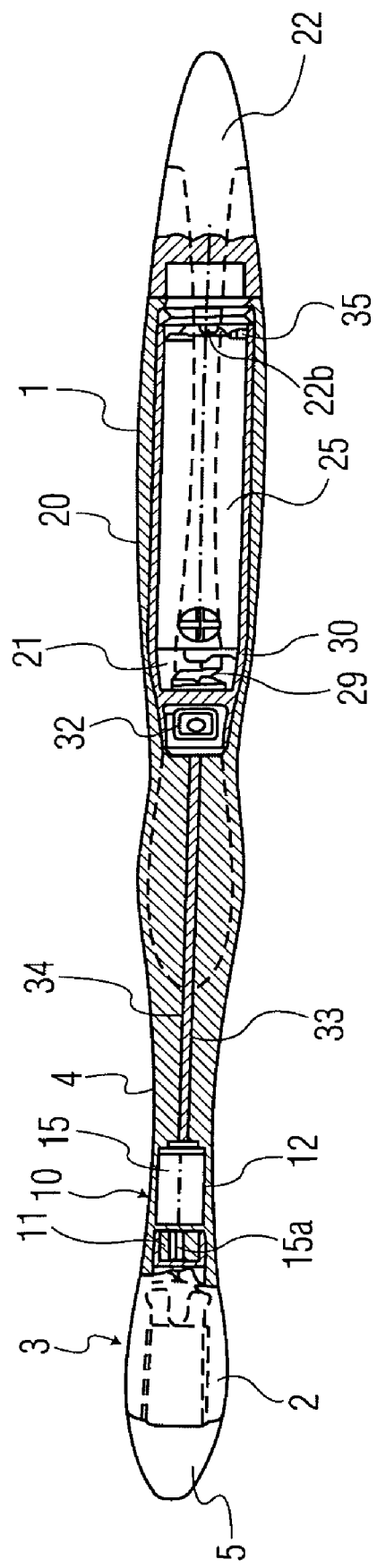
Figure 3:
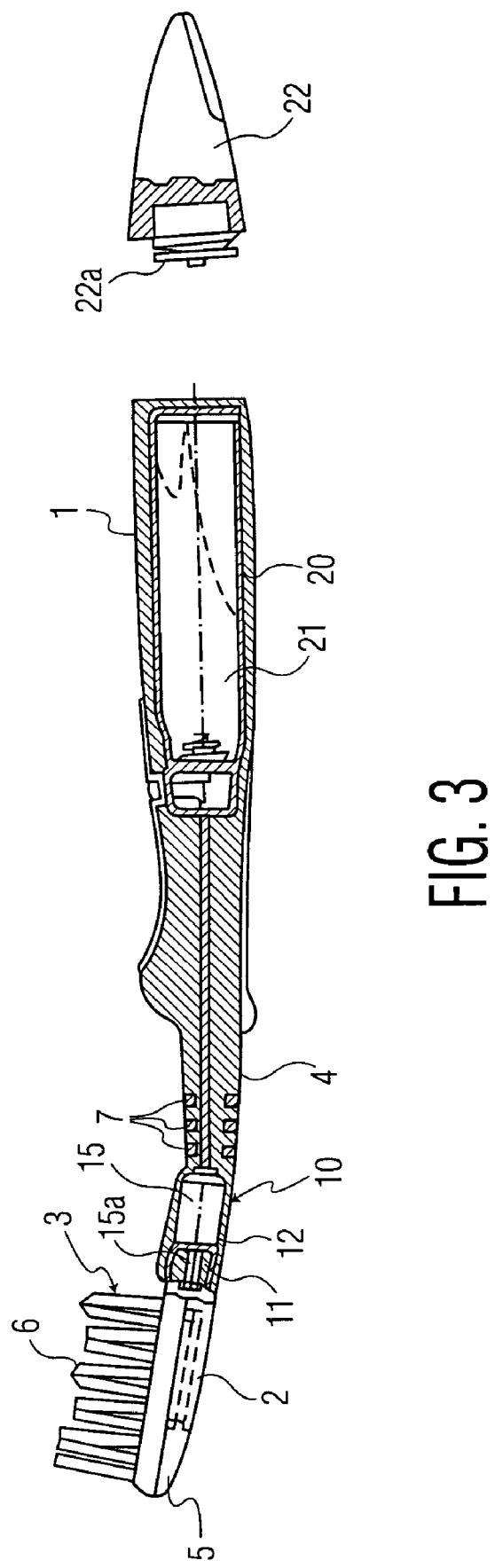
Figure 4:
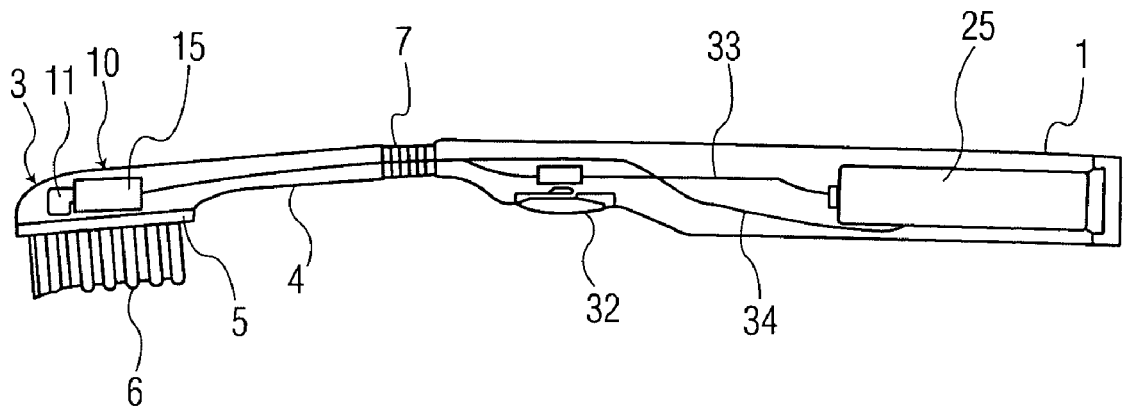
Figure 5:
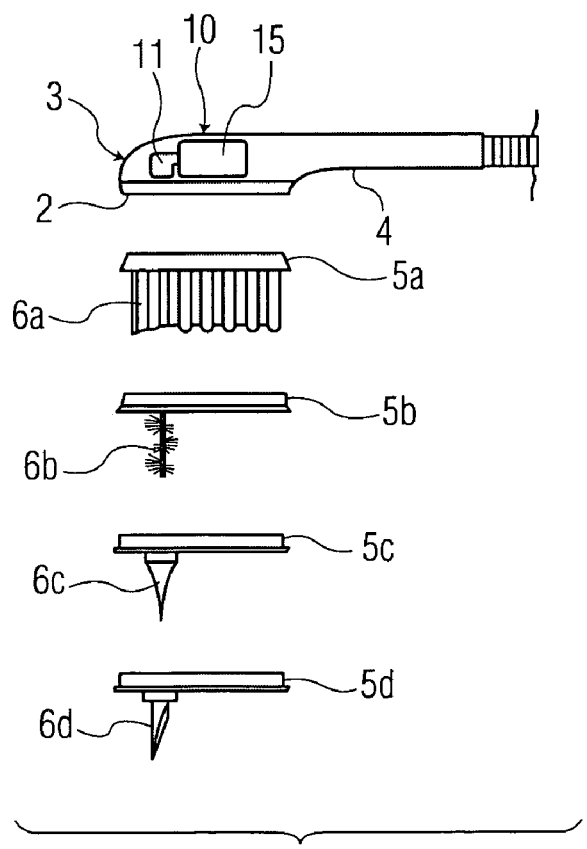

In the following detailed description, reference will be made to the accompanying drawings, wherein:

FIG. 1 shows a side view, partially in section, of a first exemplary embodiment of a toothbrush according to the invention and of a handle-closure part separated from one another (without a battery);

FIG. 2 shows a bottom view, partially in section, of a second exemplary embodiment of a toothbrush according to the invention in the assembled state;

FIG. 3 shows a side view, partially in section, of the toothbrush according to FIG. 2 and the closure part separated from one another (without a battery);

FIG. 4 shows a side view of a third exemplary embodiment of a toothbrush according to the invention in the assembled state;

FIG. 5 shows a front part of the toothbrush according to FIG. 4 with different embodiments of exchangeable treatment heads.

Figure 6:
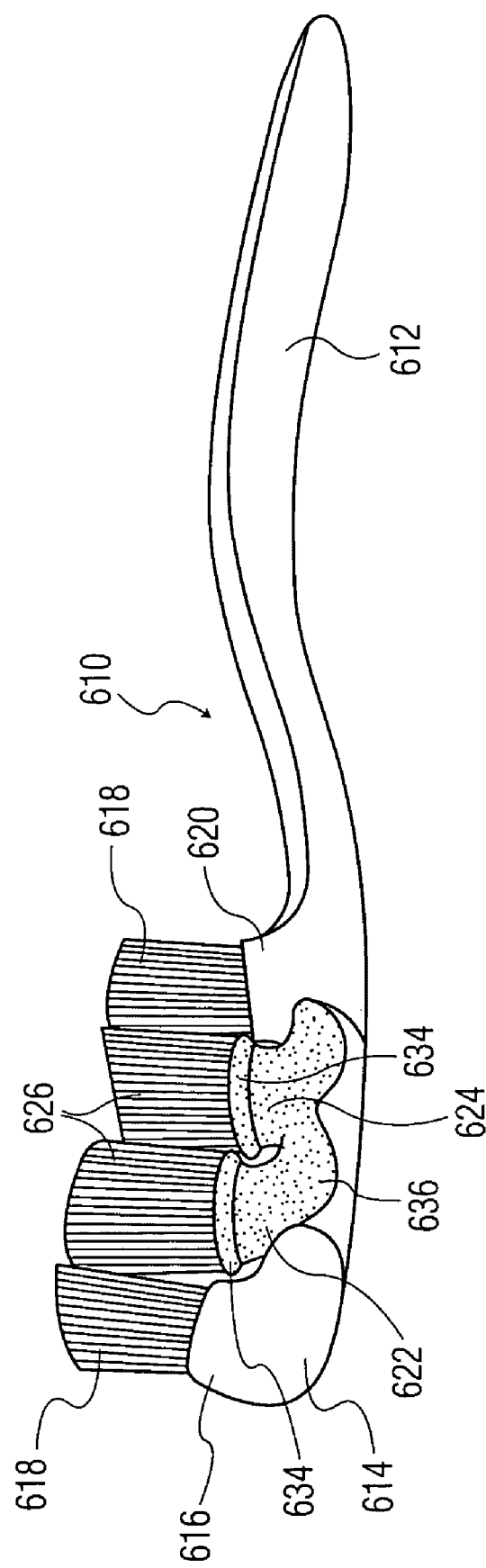
Figure 7:
Figure 8:
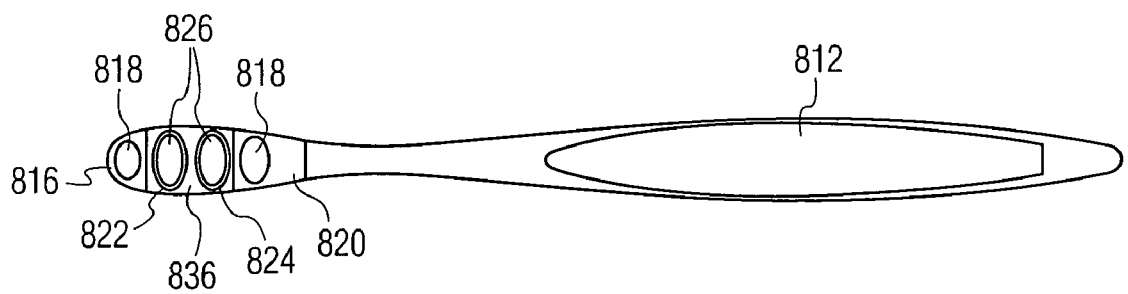
Figure 9:
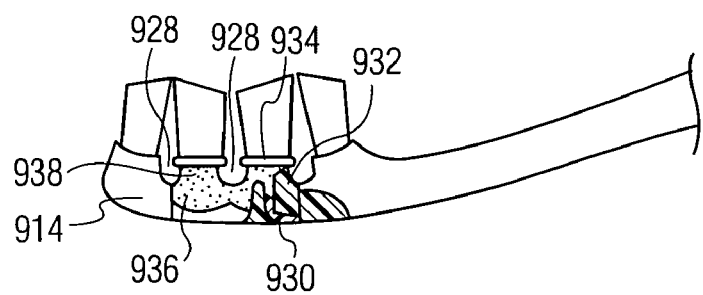
Figure 10:
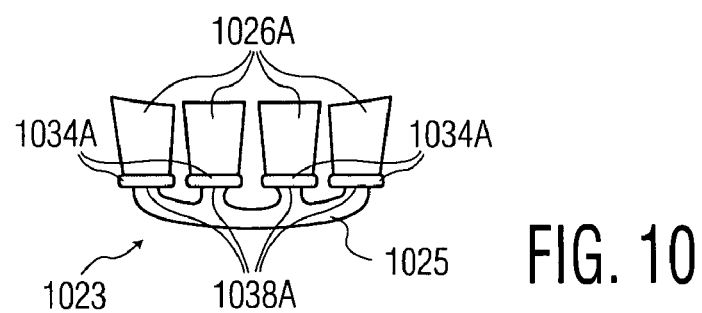
Figure 11:
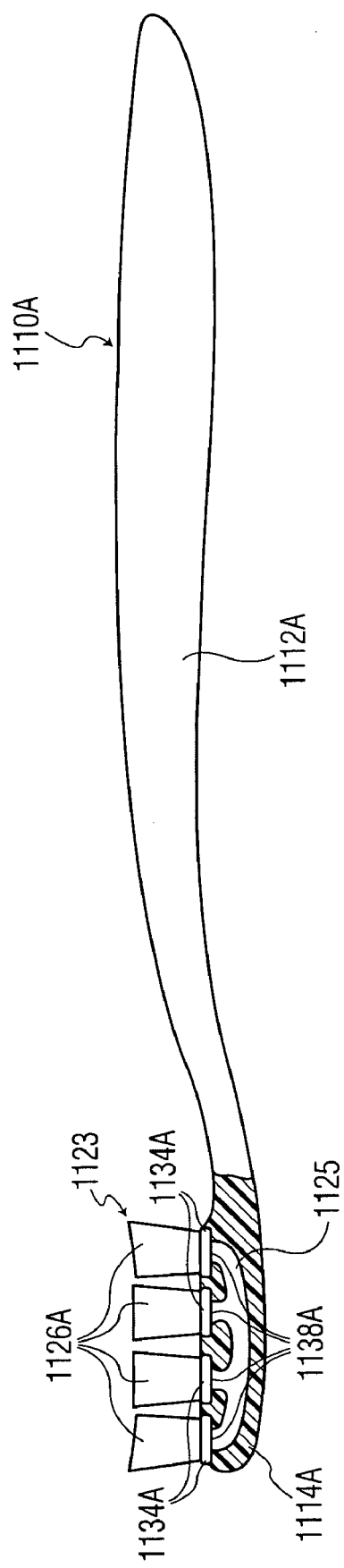
Figure 12:
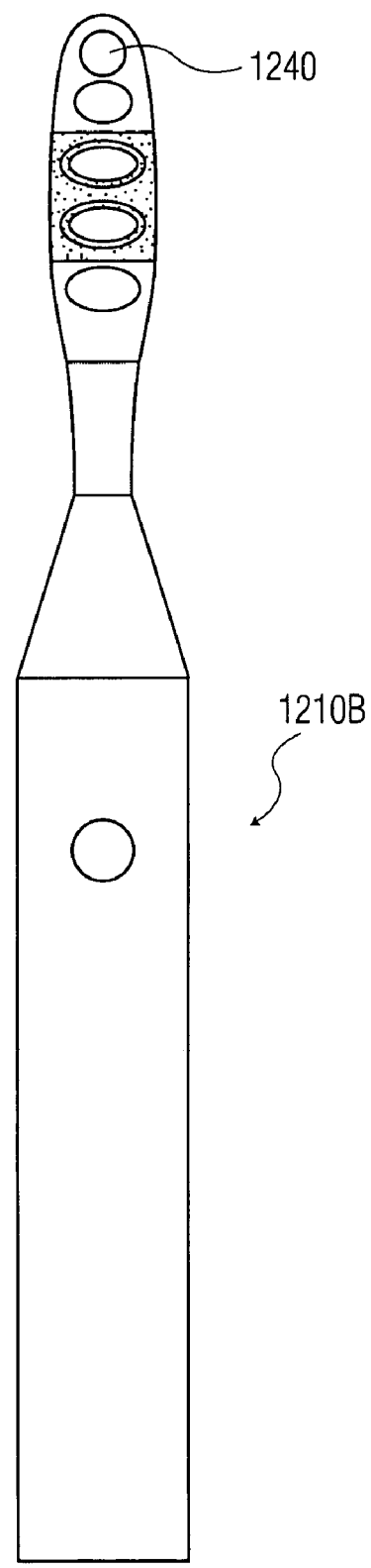

FIG. 6 is a perspective view of a toothbrush in accordance with this invention;

FIG. 7 is a side elevational view of the toothbrush shown in FIG. 6;

FIG. 8 is a front elevational view of the toothbrush shown in FIGS. 6–7;

FIG. 9 is a side elevational view similar to FIG. 7 partially broken away;

FIG. 10 is a side elevational view showing a subassembly of the bristle containing portion of the brush head in accordance with another aspect of this invention;

FIG. 11 is a side elevational view showing the subassembly of FIG. 10 incorporated in a completed toothbrush; and FIG. 12 is a front elevational view of a further toothbrush in accordance with this invention.

Figure 13:
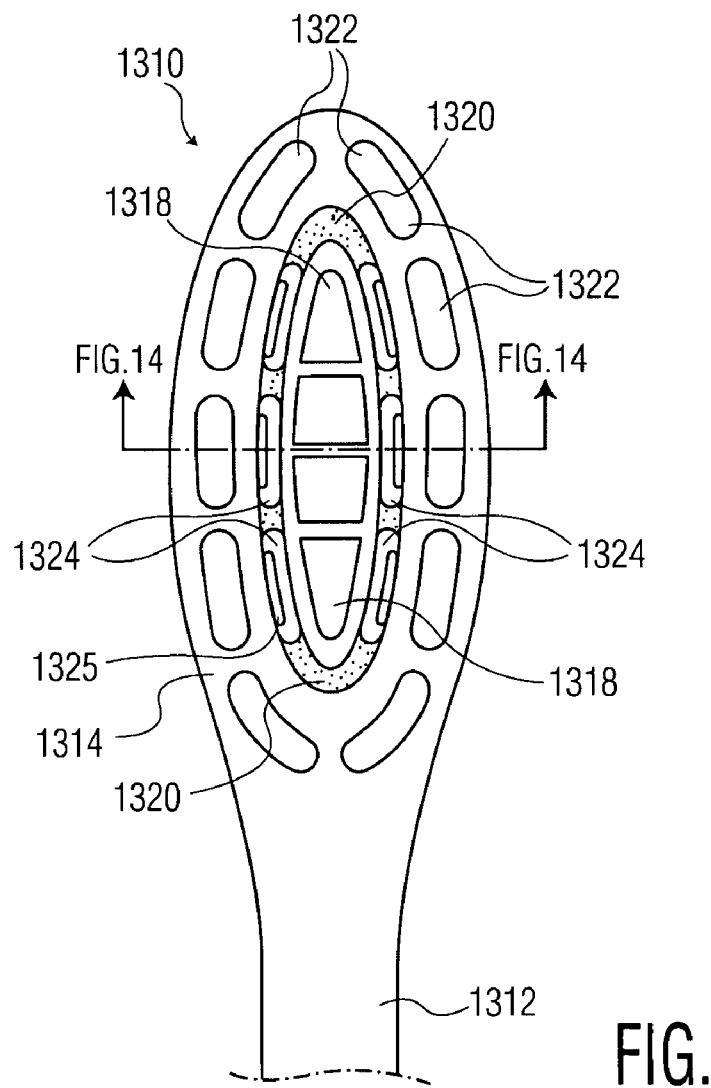
Figure 14:
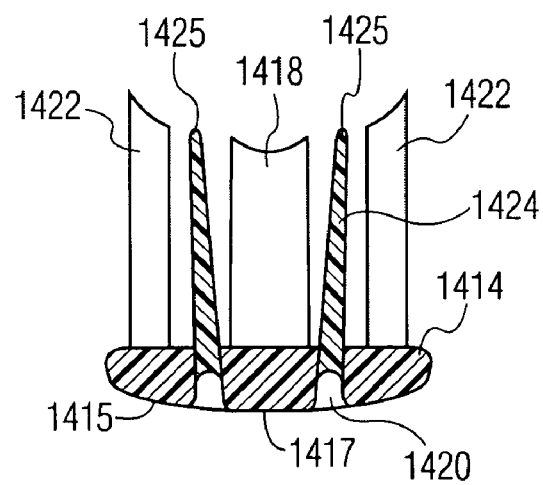

FIG. 13 is a top plan view of a manual toothbrush in accordance with this invention;

FIG. 14 is a side cross-sectional view taken along lines 2—2 of FIG. 12 showing the bristle and wiper arrangement with minimal force applied to the toothbrush handle.

Figure 15:
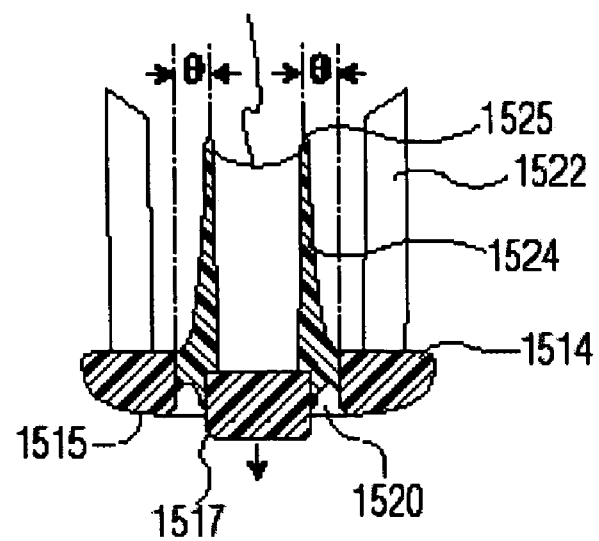
Figure 16:
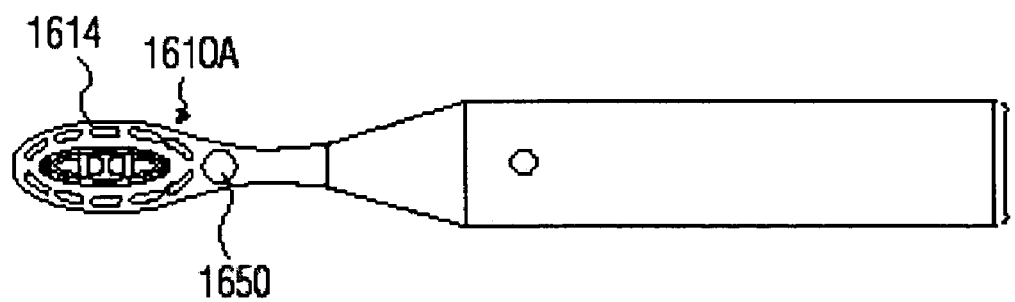

FIG. 15 is a side cross-sectional view taken along lines 2—2 of FIG. 12 showing the bristle and wiper arrangement where greater force is applied to the toothbrush handle; and FIG. 16 is a top plan view of a powered toothbrush in accordance with this invention.

Figure 17:
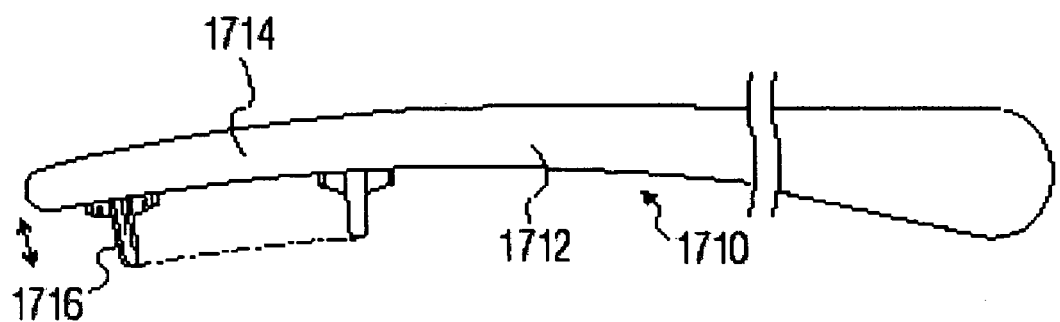

FIG. 17 is a side elevational overview of a toothbrush broken along its length having a flexible head with fingers mounted thereon, showing the ribs interconnecting the finger and flexible head.

Figure 18:
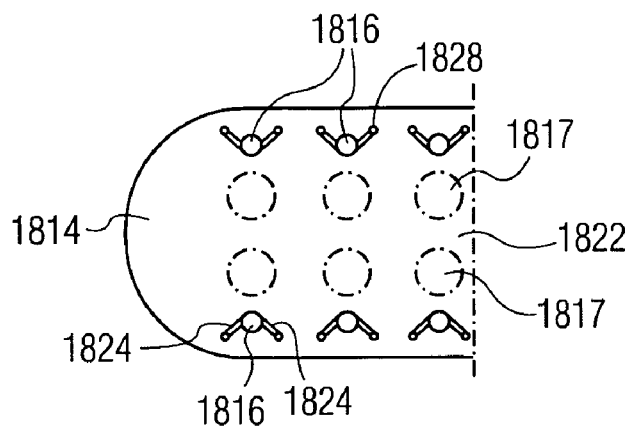

FIG. 18 is a fragmental front plan view showing an arrangement of fingers connected by ribs to a flexible head.

Figure 19:
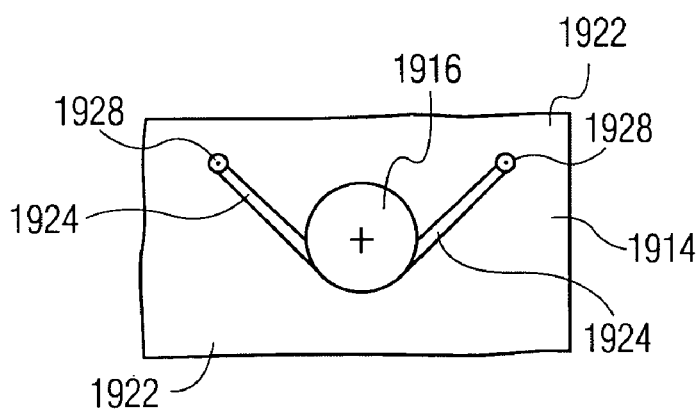

FIG. 19 is a fragmental plan view of single finger connected by ribs to an unflexed toothbrush head.

Figure 20:
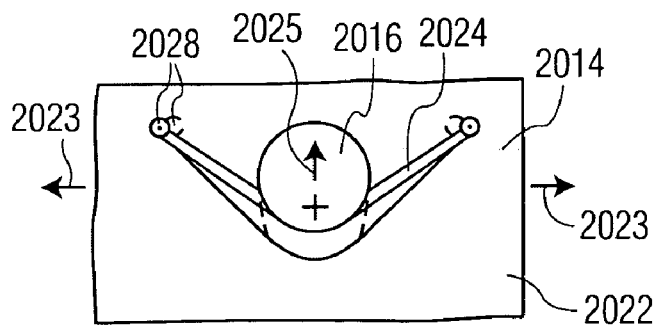
Figure 21:
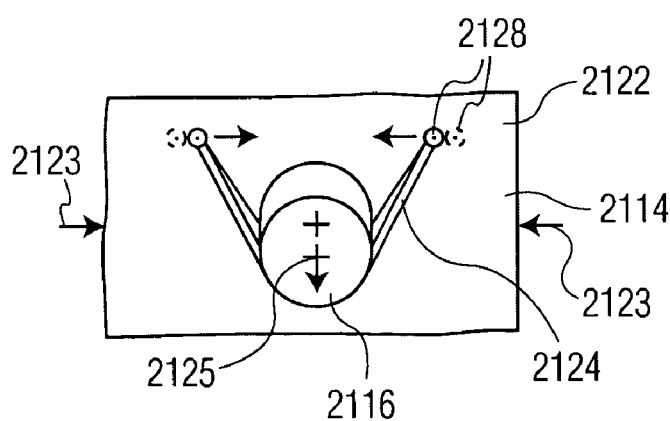

FIGS. 20 and 21 are fragmental plan views of a single finger connected by ribs to a flexible head in flexed positions caused by movement of the flexible head.

Figure 22:
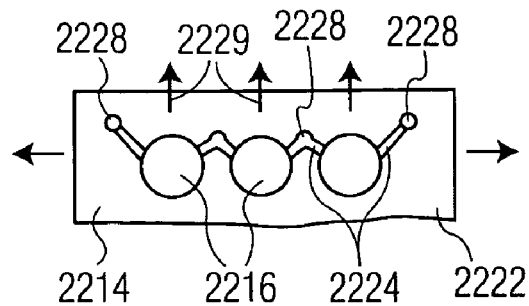
Figure 23:
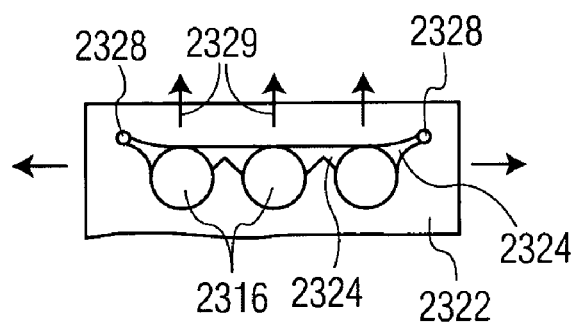
Figure 24:
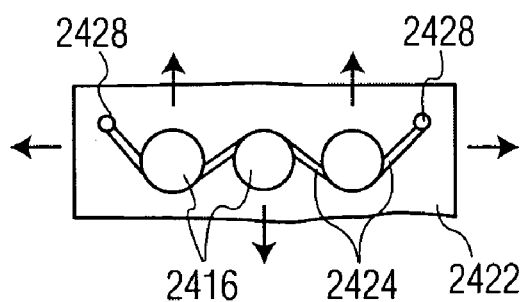

FIGS. 22–24 are fragmental plan views of multiple fingers interconnected to each other and to a flexible toothbrush head by ribs forming a web between the fingers.

Figure 25:
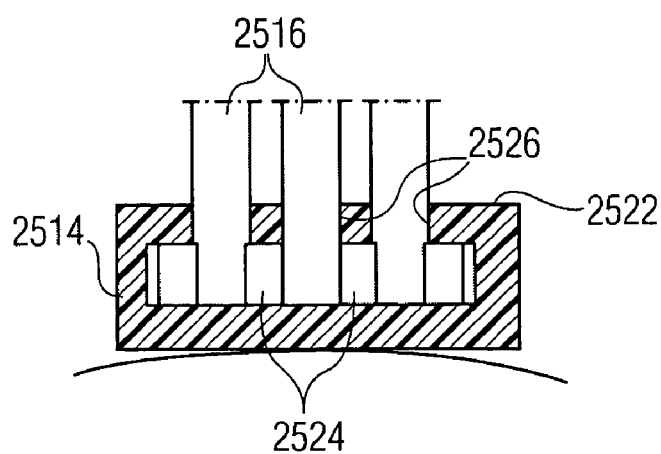

FIG. 25 is a fragmental cross-sectional view in elevation of the fingers mounted in a flexible toothbrush head.

Figure 26:
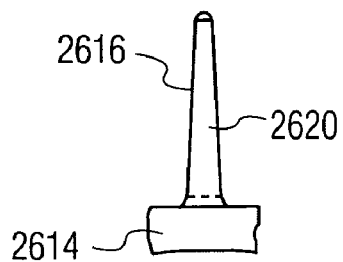
Figure 27:
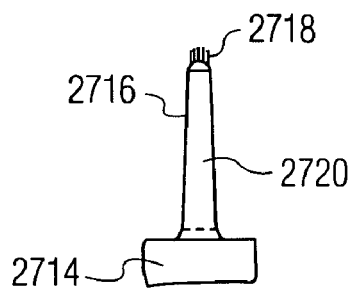
Figure 28:
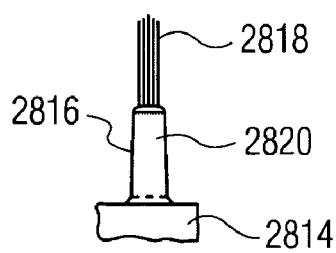

FIGS. 26–28 are fragmental elevational views of the fingers used with the toothbrush of the invention.

Figure 29:
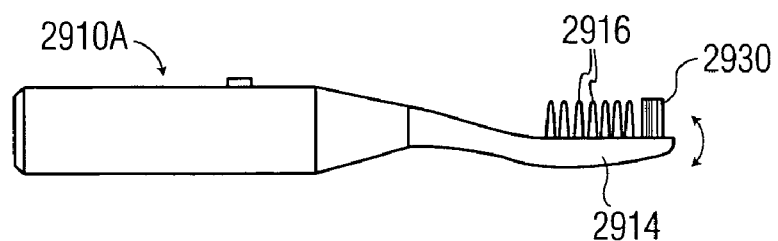

FIG. 29 is a side elevational view of a power toothbrush using a flexible head and gum stimulation fingers.

Figure 30:
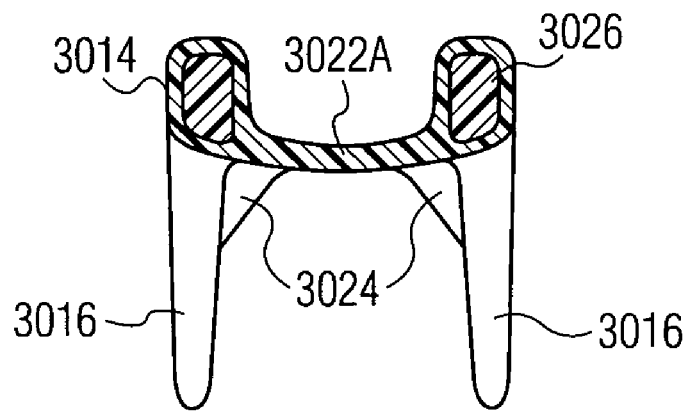
Figure 31:
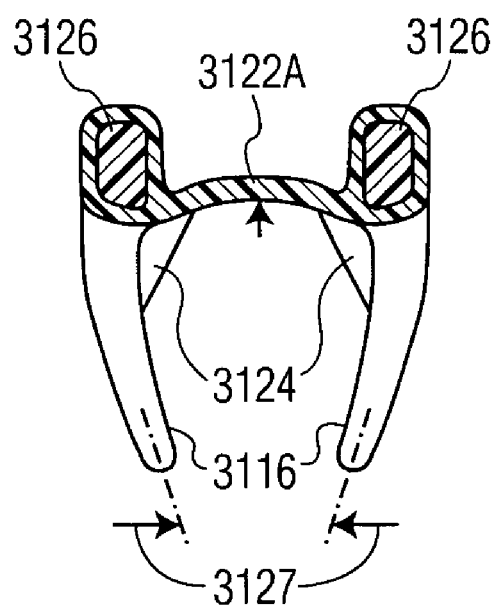

FIGS. 30 and 31 are cross sectional views of the fingers with ribs interconnecting the fingers to a flexible portion of the toothbrush head.

Figure 32:
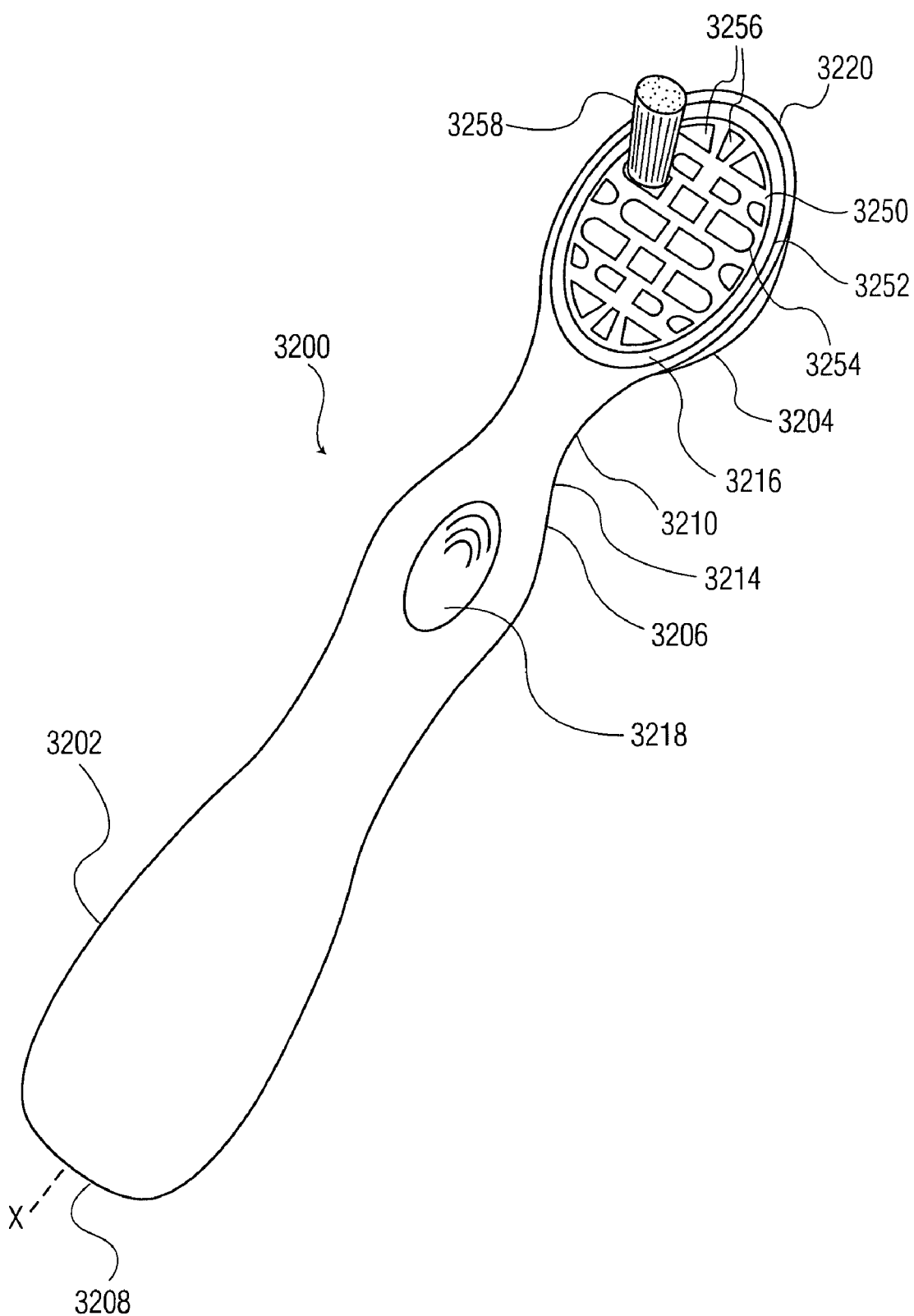

FIG. 32 is a perspective view of a toothbrush including a head constructed in accordance with a preferred embodiment of the invention.

Figure 33:
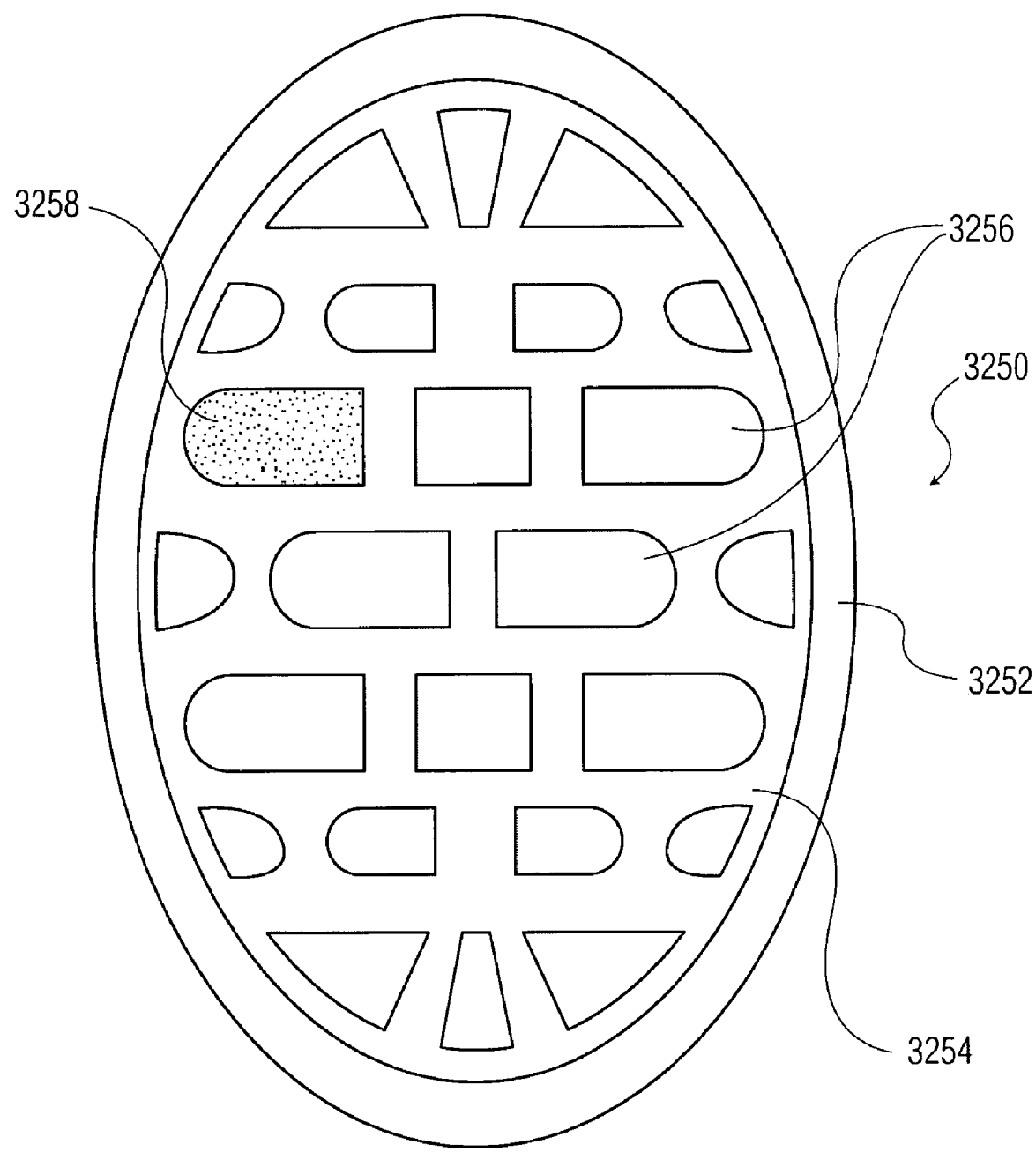

FIG. 33 is a top plan view of the head of FIG. 32.

DETAILED DESCRIPTION OF ILLUSTRATIVE PREFERRED EMBODIMENTS OF THE INVENTION

A toothbrush is provided with a mechanical vibratory element and a head having a plurality of different types of cleaning areas which provide for an enhanced cleaning effect. This application discloses a toothbrush having multiple groupings of cleaning elements uniquely mounted to the head of a toothbrush, which mounting facilitates flexible orientation of those groupings relative to the teeth and gums being cleaned. For example, the head of the subject toothbrush is designed to "wrap around" individual teeth resulting in deeper penetration of cleaning elements between teeth. This overall cleaning is accomplished by independent movement of at least two groups of cleaning elements relative to the toothbrush head and each other. The first group is a central grouping or "island" of cleaning elements flexibly mounted to the toothbrush head.

The second group is fixedly mounted to the toothbrush head in a configuration surrounding at least part of the central grouping. The central group is attached to the toothbrush head via a flexible elastomeric membrane, resilient plastic straps, webbing or other material that flexibly interconnects the first group with the toothbrush head.

In accordance with this invention the toothbrush head is divided into a plurality of separate cleaning areas. These areas include at least one and preferably two areas wherein the cleaning elements are mounted to a base with other areas having the cleaning elements mounted to pods wherein the pods have a greater degree of movability than do the bases. The pods are resilient so that during use the cleaning elements could be moved from their initial position and then returned to the initial position.

The pods may be formed from a narrow or small diameter beam extending from the body of the toothbrush head to a cleaning element support pad. Preferably the small diameter beam is enclosed in elastic material.

In a preferred practice of the invention a relatively non-movable base is located at each of the distal and proximal ends of the toothbrush head with at least two elastic pods mounted between the two bases. These various cleaning areas are separated from each other by channels extending completely across the head in a transverse direction.

In accordance with a further aspect of this invention the pods are formed utilizing an IMT process where the bristles are introduced into the mold cavity into which a plastic material is injected. As the injected material cools off, it permanently traps the bristles to form a brush. In order to achieve functional flexibility and proper tuft retention, materials are used to create a pod of mushroom shape by forming a stem and a plate to which the bristles would be secured. The pods are interconnected at the stems to form a first subassembly for making the toothbrush. This subassembly may then be attached to the bulk of the toothbrush, which includes the remainder of the head and the handle, by being overmolded with an entire toothbrush handle during a second injection cycle. As a result, the entire handle could be formed at normal speeds because the IMT process is initially isolated to a smaller material shot size.

This application further discloses a toothbrush having multiple groupings of cleaning elements ("islands") uniquely mounted to the head of a toothbrush, which mounting facilitates flexible orientation of those groupings relative to the teeth and gums being cleaned. More particularly, the bunches of cleaning elements are mounted relative to the toothbrush head using a transverse, flexible membrane or web extending from the periphery of the cleaning elements to the sidewalls of the toothbrush head.

This flexible mounting facilitates 360 degree limited angle wobble of the cleaning elements. That, in turn, orients the cleaning element towards the teeth even if the toothbrush head is not angled directly parallel to the user's teeth.

The toothbrush of this invention includes a head in the form of a base having an upstanding wall to create a peripheral frame. A thin resilient membrane or web is mounted within the frame. The membrane or web is capable of flexing to facilitate orientation of the cleaning elements carried by the membrane relative to the teeth of the user.

Preferably, the cleaning elements are bristles secured to the membrane or web by in-molded technology.

Additional cleaning elements can be arranged on the periphery of the "islands" to facilitate cleaning in those areas between the "islands". In a preferred embodiment, these additional cleaning elements are fixedly mounted to the toothbrush head outside the periphery of the membrane or web flexibly holding the "islands" of cleaning elements. This combination of flexible and fixed mounting of cleaning elements provides very effective brushing of teeth.

In use, pressure applied to the toothbrush handle by a user causes the first group of cleaning elements to contact the teeth being cleaned. As the force applied to the toothbrush exceeds a predetermined volume, the central group of cleaning elements moves relative to the balance of the head. This movement, in turn, allows the outer group of fixed cleaning elements to contact other areas of the teeth located at a greater distance from the head, including interproximal spaces between teeth.

This desired flexibility of the central grouping of cleaning elements may be accomplished with an elastomeric bridge between the central movable group of cleaning elements and the surrounding outer group of cleaning elements. This elastomeric bridge may be continuous or may be a series of independent bridges with a void between each bridge to encourage greater flexibility. The width of this bridge can be adjusted to vary the amount of force needed to push the central group of cleaning elements into a position where the outer group can achieve their greatest cleaning potential.

In another embodiment of this invention, the gap between the groups of cleaning elements corresponding to the width of the elastomeric bridge between them can effectively be filled with elastomeric wipers that move as force is applied to the central group of cleaning elements. More particularly, tapered elastomeric wipers can be mounted to the elastomeric bridge so that the narrower tip of the wipers flex inward and outward as force is applied to and released from the toothbrush handle. This wiping action further enhances the cleaning function of the disclosed toothbrush.

Turning to the Figures, both the toothbrush illustrated in FIG. 1 and that according to FIGS. 2 and 3 each have a handle 1, a front bristle-carrying head part 3 and a neck part 4, which connects the head part 3 to the handle 1. The bristles combined to form clusters of bristles 6 are anchored in a bristle carrier 5 and form a possibly profiled brushing surface with their free ends. In the embodiment illustrated, the bristle carrier 5 with the clusters of bristles 6 is positioned, in a manner which is known per se and thus is not described in any more detail, on a retaining part 2 of the head part 3 such that it can be exchanged.

The neck part 4 is provided with neck-part zones 7 which are made of an elastically relatively compliant material component and provide for, or additionally increase, the elasticity of the neck part 4, with the result that, during use of the toothbrush, the bristle-carrying head part 3 can be forced back resiliently in the case of forces acting in the direction of the brushing surface. If appropriate, the neck-part zones 7 are designed as notches which extend over part of the neck circumference and are filled with elastically compliant material (e.g. with thermoplastic elastomer). Of course, it would also be quite conceivable for the form and number of neck-part zones to be different. It is also conceivable to have a flexible neck zone without using elastic material components, e.g. by providing constrictions or by way of a bellows.

Integrated in the front head part 3, or in that region of the neck part 4 which is adjacent to the head part 3, is a mechanical vibratory device 10, by means of which vibrations which effect or enhance the teeth-cleaning action may be imparted to the bristle-carrying head part 3. The vibratory device 10 can be connected to an electric power source, accommodated in the handle 1, via electrical connections running in the neck part 4, as is described herein below. The already mentioned neck-part zones 7 made of an elastically compliant material act here as means which damp the vibration between the vibrating head part 3 and the handle 1, with the result that the vibratory action is produced, in particular, in the head part and is only transmitted to the handle 1 to a slight extent. This means that only slight vibrations can be felt in the handle 1 during the teeth-cleaning operation, and the toothbrush is thus comfortable to handle. Conversely, however, it is also advantageous that the vibration produced is not damped by the handle 1 and can act to full effect in the head part 3. Instead of the neck-part zones 7 consisting of elastically compliant material, however, other vibration-damping means would also be conceivable; it is not absolutely necessary to use an elastic material. The damping may also be achieved, using a basic material, by the neck part being configured in a particular form, for example by the presence of a bellows/accordion part, etc.

Accommodated in the handle 1 is a sheath or sleeve 20 which extends in the longitudinal direction of said handle and is made of electrically conductive material. Both the handle 1 and the sleeve 20 are open to the rear, this forming a cavity 21 which can be closed from the rear by a closure part 22 and into which it is possible to insert a battery 25, in the exemplary embodiment illustrated a commercially available, non-rechargeable cylindrical battery, with a defined power (e.g. 1.5 V) as the power source for the vibratory device 10. It would also be possible, however, for a button cell or for a rechargeable storage battery to be used as the power source.

A spring contact 29 for the positive pole 30 of the battery 25 (see FIG. 2) is fitted in the sleeve 20, on a transverse wall 28, and is connected to the vibratory device 10 via an electric line 31, a switch 32, which is installed in the sleeve 20 and can be actuated from the outside of the handle 1, and an electric line 33 running in the neck part 4. The electrical connection can be interrupted by means of the switch 32.

The closure part 22 is provided with a threaded stub 22a made of an electrically conductive material and can be screwed into the handle 1 and/or into the sleeve 20 by way of said threaded stub. The threaded stub 22a is provided with a contact surface 22b which, with the closure part 22 screwed in, comes into abutment against the negative pole 35 of the battery 25 inserted into the sleeve 20. The negative pole 35 is electrically connected to the vibratory device 10 via the threaded stub 22a, the sleeve 20 itself and a line 34, which connects the sleeve 20 to the vibratory device 10 and runs in the neck part 4.

Instead of being transmitted via the electrically conductive sleeve 20, it would also be possible for the power to be transmitted in some other way, for example using wires or an electrically conductive plastic.

In the exemplary embodiment illustrated in FIG. 1, the vibratory device 10 comprises a vibratory element 11' which functions preferably in the manner of a vibratory armature, can be electrically connected directly to the power source via the lines 33, 34 and, with the power source connected, is made to vibrate.

In the case of the toothbrush variant illustrated in FIGS. 2 and 3, the vibratory device 10 comprises a vibratory element 11 in the form of an eccentric, which produces mechanical vibrations and can be rotated about an axis located in the longitudinal direction of the toothbrush, and also comprises a drive which is arranged directly adjacent and is designed as a micromotor 15. The vibratory element 11 is connected to the shaft 15a of the micromotor 15, which can be electrically connected to the power source via the lines 33, 34. The micromotor 15 and the eccentric may be accommodated as a structural unit in a housing 12.

Instead of an eccentric which can be driven in rotation, it would also be possible to have a vibratory element 11 which can be driven in a translatory manner.

It would be possible, in the case of the toothbrush according to the invention, to arrange the bristle-carrying head part 3 such that it can be moved in relation to the neck part 4 in order for the latter, in the case of vibrations produced by means of the vibratory device 10, to be made to move in relation to the rest of the toothbrush.

The electric lines 31, 33, 34 could also be realized by electricity-conducting plastic tracks.

The switch 32, which connects or interrupts the lines 31, 33, may also be, for example, a magnetic switch.

The preferred configuration of the switch 32, however, contains a pulse switch arranged on a printed circuit board as well as further electronic components which store the switching state.

It is also possible, however, for the electrical connection between the battery 25 and the vibratory element 11' (FIG. 1) or the drive 15 (FIGS. 2 and 3) to be produced or interrupted not by the switch 32, but by the closure part 22, which can be screwed into the handle 1 and/or into the sleeve 20 or connected to the same in a bayonet-like manner, being turned (i.e. the switch 32 is dispensed with in the case of such a configuration).

Instead of the rear closure part 22 being screwed to the handle 1, it would, of course, also be possible to have some other type of releasable connection (e.g. plug-in connection, bayonet connection, etc.) and a corresponding configuration of the contact part interacting with the negative pole 35.

It would also be possible for the closure part 22 to be in a form which is quite different to that illustrated in the drawing. For example, the closure part could be provided with a set-down surface or a foot part and thus serve as an element on which the toothbrush can be set down.

The toothbrush illustrated in FIG. 4 corresponds essentially to that according to FIGS. 2 and 3; the same parts, once again, have the same designations. According to FIG. 4, the vibratory device 10 is arranged directly in the front head part 3. In this exemplary embodiment, the sleeve 20 is dispensed with; the battery 25 is connected directly to the vibratory device 10 via the lines 33, 34. It is also the case with this toothbrush that use is preferably made of an exchangeable bristle carrier 5 which can be positioned on a retaining part 2 of the head part 3, e.g. in the manner of a snap-in connection. The capacity for changing the bristle carrier 5 provided with the clusters of bristles 6 is particularly advantageous since the toothbrush provided with the vibratory device 10 can be used irrespective of the service life of the bristles, which is usually even shorter than the service life of the battery 25.

As can be seen from FIG. 5, it is possible, instead of the bristle carrier 5 or 5a, which forms part of a conventional brush head and is provided with respective clusters of bristles 6 or 6a, to position other, optionally different bristle carriers or adapters 5b to 5d on the retaining part 2, these being provided with different interdental brushes 6b, 6c or interdental treatment parts 6d for effective cleaning of the spaces between the teeth. The interdental brush 6b may be designed, for example, as a helical brush made of coated wire with plastic filaments twisted in. The interdental brush 6c comprises bristles which, together, form a cluster tip. The treatment part 6d may be designed, for example, as a plastic element which has a tip and may preferably be provided with an abrasive coating for removing plaque and tartar from the spaces between the teeth. Of course, it would also be possible to use any other desired treatment heads.

It is also the case with the variant according to FIGS. 4 and 5 that the bristle carrier 5 could be configured such that a vibration-induced movement in relation to the retaining part 2 were possible.

For the introduction of the vibratory device 10, the connecting lines 33, 34 and further electronic components, it is possible for the toothbrush according to the invention, or the housing thereof, to be produced in two parts and for the two parts to be welded in a water-tight manner once the abovementioned parts have been positioned therein.

It is also possible, however, for the toothbrush according to the invention to be produced by injection molding preferably involving two or more components. The abovementioned parts are advantageously positioned as a unit in an injection molding made of a first material component and then encapsulated in the second material component (or in the further material component) by injection molding. It is not necessary here for full encapsulation to take place. Certain parts may be exposed, as a result of which it is possible to achieve an esthetic effect.

It would also be possible, however, for the abovementioned electronic components to be inserted into a ready molded handle 1.

Since it is not only the vibratory element 11, 11' itself but also the drive, i.e. the micromotor 15, which are arranged in the front head part 3, or in the directly adjacent front region of the neck part 4, it is not necessary for any mechanical drive means to be led through the flexible neck part 4 in order to connect the micromotor to the vibratory element 11. It is only the electric lines 33, 34 (wires, cables or electrically conductive plastic tracks) which run through the neck part 4.

According to the invention, use is made of a mechanical vibratory device 10 which has a diameter of less than 15 mm, preferably less than 6 mm, and is less than 35 mm, preferably less than 20 mm, in length. This ensures that the toothbrush may be of ergonomic configuration and is easy to handle. The toothbrush according to the invention corresponds, in size, more or less to the conventional manual toothbrushes, which makes them more straightforward to handle in comparison with the commercially available, considerably larger electric toothbrushes, even though this toothbrush achieves a cleaning action which is comparable with that of the known electric toothbrushes, but is gentler than the latter. Moreover, the toothbrush according to the invention is straightforward and cost-effective to produce.

A number of head configurations can produce a enhanced cleaning effect when the mechanical vibratory device is engaged.

FIGS. 6–9 illustrate a toothbrush 610 in accordance with one aspect of this invention. As shown therein toothbrush 610 includes an elongated hand-held handle 612 with a head 614 connected to and extending from the handle. The head 614 is divided into a plurality of separate cleaning areas which are spaced from each other. As illustrated the cleaning areas include a base 616, 816 located at the distal end of the head 614 and projecting outwardly from the main body portion 930 of the head. Base 616, 816 includes at least one and preferably a plurality of cleaning elements 618, 818. Head 614 further includes a base or supporting member 620, 820 at the proximal end of head 614. Cleaning elements 618, 818 also extend outwardly from base 620, 820.

Mounted between the cleaning areas which incorporate bases 616, 816 and 620, 820 are a pair of pods 622, 822, 624, 824. Each pod is provided with at least one and preferably a plurality of cleaning elements 826. As later described the pods 622, 822, 624, 824 have a greater degree of movability than do the bases 616, 816, 620, 820. In the preferred practice of the invention the pods 622, 822, 624, 824 are resilient members so that the pod cleaning elements add a motion range beyond the cleaning elements 618, 818 which are generally static or non-movable. Preferably, because the various cleaning elements are separated from each other such as by channels 728, 928 which extend completely across head 614 in a transverse direction and because of the elastic nature of pods 622, 822, 624, 824, the cleaning elements 626, 826 are capable of 360 degrees rotation about the vertical axis of each individual pod. The angle of the bend is dictated by the ability of the material to bend.

Toothbrush 610 thus provides a head 614 wherein the front (distal end) and the back (proximal end) areas are in a relatively fixed position and wherein the cleaning elements, such as bristle strands, 618, 818 do not have any extra degree of motion. The middle portion of head 614, however, has two areas of cleaning elements 626, 826 which are capable of 360 degree rotation.

As best shown in FIG. 9 the head 914 includes a main body portion 930 which supports the bases and pods. Body portion 930 and bases 616 and 620 are preferably made from conventional hard plastic materials, such as polypropylene, commonly used in the making of toothbrush handles and heads. Pods 622, 822, 624, 824, however, are made so as to be resilient. In the preferred practice of this invention, the resiliency of pods 622, 822, 624, 824 is achieved by providing a thin diameter beam 932 which extends from the main body portion 930 of the head of the toothbrush. Beam 932 is joined into the bottom of a thin pad or plate 934 which provides a support area onto which the cleaning elements 626, 826 are affixed. The manner of mounting the cleaning elements 626, 826 to the support pads 934 can be achieved utilizing various cleaning elements, such as bristles and other cleaning materials, in known attachment methods.

The desired flexibility or resiliency of the pods 622, 822, 624, 824 is enhanced by enclosing the thin beams 932 in elastic material 636, 836, 936 which could be acquired during the multi-injection molding process. The elastic material 636, 836, 936 serves as a rubber band by returning the beams 932 to their original form or initial position. This return action creates an active motion in the opposite direction of the beam bend which aids in the cleaning of teeth by introducing extra brushing strokes.

As best shown in FIGS. 6, 7 and 9 the pods 622, 822, 624, 824 include a widened portion disposed toward the body 930. The support pads 934 are also widened. Each pod has a narrow or reduced diameter central portion 938 longitudinally intermediate the length of each pod. Thus, each pod is of generally mushroom shape.

Beam 932 could be of any suitable shape such as having a cross-section which is circular, square or any other geometric shape that provides a thin dimension or thin diameter to the beam to facilitate the bendability of the beam. The elastomer 636, 836, 936 may be considered as a continuous layer of any suitable thickness which covers the entire central area of head 614, 914 as illustrated so that both pods 622, 822, 624, 824 are incorporated as part of the same elastic material. The portion of the head 614, 914 which includes pods 622, 822, 624, 824 may be formed as a separate subassembly similar to the subassembly later described with respect to FIGS. 10 and 11.

Although the invention could be practiced with a single base and a single pod and could be practiced with the base having some, but a lesser degree of flexibility than the pod, the invention is preferably practiced wherein the base is generally static or non-movable. In addition, the invention is preferably practiced where there are a plurality of such bases and a plurality of pods. The drawings illustrate a preferred practice of the invention where there are a total of four separate cleaning areas with the pods being located in the central portion of head 614, 914. The invention is also preferably practiced where the cleaning elements comprise a plurality of bristles or strands on each base and each pod.

As illustrated in FIG. 8 each base 816 and 820 and each pod 822 and 824 has a generally oval outer surface. The bases and pods are longitudinally aligned, but spaced from each other by the depressions or open areas which form the channels 728, 928. As also illustrated in FIG. 8 the pods have a larger outer surface or cleaning element carrying surface than do the bases.

As shown in FIG. 7 the terminal surfaces of the cleaning elements 618 and 626 are tapered so that the terminal surfaces of the cleaning elements 618 taper outwardly in a direction toward the center of head 614 while the terminal surfaces of cleaning elements 626 taper outwardly in a direction away from the center of head 614. Thus, the highest points of each set of cleaning elements 618 and its adjacent set of cleaning elements 626 are generally disposed toward each other for each pair of base and pod 616, 622 and 620, 624.

Any suitable form of cleaning elements may be used as the cleaning elements 618 and 626 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions. Where bristles are used, the bristles could be mounted to tuft blocks or sections by extending through suitable openings in the tuft blocks so that the base of the bristles is mounted within or below the tuft block.

Using different cleaning materials as cleaning elements of the toothbrushes may yield different effects. In an attempt to provide better stain removal a rubber-like material or elastomer can be used in combination with conventional bristles or used by itself to "brighten/whiten" the teeth.

It is to be understood that the specific illustration of the cleaning elements is merely for exemplary purposes. The invention can be practiced with various combinations of the same or different cleaning element configurations (such as stapled or in-molded technology bristles, etc.) and/or with the same bristle or cleaning element materials (such as nylon bristles, spiral bristles, rubber bristles, etc.) Similarly, while FIG. 7 illustrates the cleaning elements to be generally perpendicular to the outer surface of head 614, some or all of the cleaning elements may be angled at various angles with respect to the outer surface of head 614. It is thereby possible to select the combination of cleaning element configurations, materials and orientations to achieve specific intended results to deliver additional oral health benefits, like enhanced cleaning tooth polishing, tooth whitening and/or massaging of the gums.

FIGS. 10–11 illustrate a further aspect of this invention relating to techniques for forming the toothbrush. The toothbrush 1110A has the ability to provide flexible support for the bristles 1026A, 1126A in designated areas. The flexibility is provided by designing the tuft holding areas 1034A, 1134A as plates which in combination with the stems 1038A, 1138A forms pods of mushroom shape. The mushroom stem 1038A, 1138A is made flexible to allow the plate 1034A, 1134A populated with bristles or cleaning elements 1026A, 1126A to move in different directions while brushing, as described with respect to the flexible pods of FIGS. 6–9.

FIGS. 10–11 show the toothbrush 1110A and in particular the cleaning element or bristle carrying portion 1023, 1133 of the head 1114A to be made utilizing an IMT process. As shown in FIG. 10 the bristle or cleaning element carrying portion 1023 forms an initial subassembly. This subassembly is made by introducing the cleaning elements 1026A into the mold cavity into which a plastic material is injected. As the material injected cools off it permanently traps the bristles or cleaning elements 1026A to form a brush or subassembly 1023.

To achieve a functional flexibility and proper tuft retention the portion of the bristle holding part or subassembly 1023 which comprises the plates 1034A, stems 1038A and interconnecting support 1025, 1125 is preferably a blend of polypropylene (PP) and soft TPE. Once the PP/TPE blend is combined with the bristles 1026A the subassembly 1023 is formed. In an initial independent IMT step the subassembly 1023 is then overmolded with an entire toothbrush handle 1112A and head 1114A during a second injection cycle to form the completed toothbrush 1110A shown in FIG. 11. If desired or required the entire handle 1112A and head 1114A absent the subassembly 1123 could be made first and the subassembly or bristle retaining portion 1123 made second.

Other IMT toothbrushes that have bristles attached to the bulk of the handle as known in the prior art are difficult to make because of the slow injection speed needed to fill the head of the toothbrush. The present invention permits the making of an entire handle at normal speeds by isolating the IMT process for making subassembly 1023, 1123 to the smaller material shot size. Although a blend of PP/TPE is a preferred practice of this invention such blend is not required to make an IMT brush using the method of this invention. Similarly, the invention may be practiced using compatible materials to fuse the first and second shots so that the subassembly 1023, 1123 created in one of the shots will be secured to the remainder of the toothbrush in the other shot. Thus, the two shots are mechanically trapped together to achieve essentially the same benefits as achieved by combining the subassembly 1023, 1123 with the remainder of the toothbrush in a second injection cycle.

It is to be understood that the invention described in FIGS. 10–11 could be practiced where all portions of the head 1114 include the flexible mushroom sections without having less flexible base portions such as bases 616, 816 and 620, 820 of FIGS. 6–9. Similarly, the subassembly two shot techniques of FIGS. 10–11 could be utilized in the embodiment of FIGS. 5–9 for forming the two or more central pods as a single subassembly initially made separate from the remainder of the toothbrush head 1114. The final toothbrush would be made in a second injection molding process wherein the subassembly having interconnected pods 622, 822, 624, 824 would be molded to the handle 612, 812, 1112 and head 614, 914, 1114 made of more rigid material.

As noted, FIG. 7 illustrates the terminal surfaces of the cleaning elements 618 and 626 to be tapered in an up and down or zig zag manner. FIGS. 10–11 show an alternative taper wherein the terminal surfaces form a smooth, gentle, concave shape. If desired, other shapes may be used such as a planar shape for the terminal surfaces or a convex shape as well as the zig zag or up and down shape shown in FIG. 7. Similarly, the terminal ends of the cleaning elements in the FIGS. 6–9 embodiment, as well as those of FIGS. 10–11, could have the various shapes such as zig-zag, convex, concave or planar.

Although FIGS. 6–9 and 10–11 illustrate a manually operated toothbrush, the invention may also be practiced where the head includes one or more power or electrically operated movable sections carrying cleaning elements. Such movable section may oscillate in a rotational manner or may oscillate linearly in a longitudinal direction with respect to the longitudinal axis of the head or may oscillate linearly in a lateral or transverse direction with respect to the longitudinal axis of the head. The movable section may oscillate in and out in a direction toward and away from the outer surface of the head. The movable section may rock back and forth with respect to the outer surface of the head. The movable section may rotate continuously in the same direction, rather than oscillate. Any suitable drive mechanism may be used for imparting the desired motion to the movable section. Where plural movable sections are used, all of the movable sections may have the same type and direction of movement, or combinations of different movements may be used.

FIG. 12 illustrates a toothbrush 1210B which includes a power driven movable disc or section 1240 having cleaning elements. The movable section 1240 could be oscillated rotationally such as by using the type of drive mechanism shown in U.S. Pat. No. 5,625,916, or could move in and out using the type of drive mechanism shown in U.S. Pat. No. Re. 35,941, all of the details of both patents are incorporated herein by reference thereto. Alternatively, the other types of drives referred to above could move section 1240 in other manners and directions. Although FIG. 12 shows movable section 1240 to be at the distal end of the head, the movable section(s) could be located at any desired location on the head.

FIGS. 13–15 illustrate the head 1314–1614 of a manual toothbrush 1310 in accordance with this invention which would be attached to a handle 1312 (partially shown in FIG. 13). This invention is primarily directed to the arrangement of two groups of cleaning elements or bristles. The first group as illustrated in FIG. 13 is located in the central region of the head 1314–1614 and comprises cleaning elements 1318 in the form of strands or bristles attached via in-molded technology (IMT) methods that generally require small cross-sections of material into which the strands are permanently attached. The strands utilizing IMT methods are preferably attached during formation of the toothbrush handle or at least during formation of the head which is the portion of the toothbrush to which the strands and other materials are attached.

The first group of cleaning elements 1318 is preferably mounted in a central movable portion 1517 of head 1514 that may be deflected downward in the direction of the arrow shown in FIG. 15 when a certain force is applied to the toothbrush handle. This movement of the central portion 1517 of head 1514 is facilitated by the flexible attachment of central portion 1517 to the balance of the head by elastomeric or other flexible material 1520. The elastomeric material 1520 bridges the gap between the central movable portion 1517 of head 1514 and the rigid portion 1415 of the head as illustrated in FIGS. 14 and 16.

The elastomeric material 1320, 1420, 1520 should be a material or combinations of material that can flex to become altered from its original shape and recover to its original shape randomly during brushing.

The first group of cleaning elements 1318, 1418, 1518 flexibly mounted in head 1314, 1414, 1514, 1614 are complemented by a second group of fixed cleaning elements 1322, 1422, 1522 generally arrayed in a surrounding relationship with the first group 1318, 1418, 1518.

The first and second group of cleaning elements work together as follows to provide improved cleansing of teeth. As illustrated in FIGS. 14 and 15 when minimal force is applied to toothbrush 1310 the end of the central group of cleaning elements 1418, 1518 facing the toothbrush user extend approximately the same distance from head 1414, 1514 as the outer or fixed group of cleansing elements 1422, 1522. When additional force is applied to the toothbrush, the center moveable portion 1517 of head 1514 slightly displaces downward (see FIG. 3). This facilitates deeper penetration of the second group of cleaning elements 1422,1522 into the interproximal areas between teeth where plaque and food deposits can cause decay.

To further promote teeth cleaning, the toothbrush 1310 of this invention may include wipers 1324 positioned between the two groups of cleaning elements as best illustrated in FIG. 13. These wipers are preferably made of rubber or like material with a typical cross-section as illustrated in FIGS. 14 and 15. These wipers 1424, 1524 extend radially from head 1414, 1514 and are preferably mounted on the flexible elastomeric material 1420, 1520 that bridges the gap between the first 1418, 1518 and second 1422, 1522 groups of cleaning elements. The outer ends 1425, 1525 of wiper 1424, 1524 will move inward toward each other upon application of force to the toothbrush due to the downward displacement of the movable portion 1417, 1517 of head 1414, 1514. As illustrated in FIG. 15 this downward displacement of movable portion 1517 of head 1514 causes the outer ends 1525 of wipers 1524 to sweep across the teeth thereby further enhancing the cleansing action of toothbrush 1310. Upon reduction of force on the toothbrush the movable portion 1517 of head 1514 moves back to its normal position, causing the ends 1525 of wipers 1524 to rotate back across the teeth. The extent of the sweeping motion of ends 1525 of wipers 1524 can be controlled by the location of the wipers relative to the placement of the elastomeric material 1520 between the two groups of cleaning elements.

Any suitable form of cleaning elements may be used as the cleaning elements 1318, 1418, 1518 and 1322, 1422, 1522 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions.

It is to be understood that the specific illustration of the cleaning elements is merely for exemplary purposes. The invention can be practiced with various combinations of the same or different cleaning element configurations (such as stapled or in-molded technology bristles, etc.) and/or with the same bristle or cleaning element materials (such as nylon bristles, spiral bristles, rubber bristles, etc.) Similarly, while FIGS. 13–15 illustrate the cleaning elements to be generally perpendicular to head 1314, 1414, 1514, some or all of the cleaning elements may be angled at various angles with respect to the outer surface of head 1314, 1414, 1514. It is thereby possible to select the combination of cleaning element configurations, materials and orientations to achieve specific intended results to deliver additional oral health benefits, like enhanced cleaning, tooth polishing, tooth whitening and/or massaging of the gums.

This invention may also be practiced where the head 1314, 1414, 1514 includes one or more power or electrically operated movable sections carrying cleaning elements.

FIG. 16 illustrates a toothbrush 1610A which includes a power driven movable disc or section 1650 having cleaning elements. The movable section 1650 could be oscillated rotationally such as by using the type of drive mechanism shown in U.S. Pat. No. 5,625,916, or could move in and out using the type of drive mechanism shown in U.S. Pat. No. Re35,941; all of the details of both patents are incorporated herein by reference thereto. Alternatively, the other types of drives referred to above could move section 50 in other manners and directions. Although FIG. 16 shows movable section 1650 to be at one end of the head, the movable section(s) could be located at any desired location on the head.

FIGS. 17 and 18 illustrate a toothbrush 1710 with a handle 1712 and head 1714, 1814. Mounted on or in head 1714, 1814 are fingers 1716, 1816, preferably having a tapered shape. As shown in FIG. 18 fingers 1816 are preferably arranged about the periphery of head 1814. That location materially assists the gum massaging effect of the finger movement contemplated by this invention. More particularly, when the longitudinal axis of toothbrush 1710 is perpendicular to the axis of teeth being brushed, as is typical with most users, the fingers 1716, 1816 are closest to the gumline.

The fingers 1716, 1816 are preferably flexible and soft to the touch. Accordingly they may be formed of a soft elastomeric material. The general shape of fingers 2616, 2716, 2816 is illustrated in FIGS. 26–28. As so illustrated they are tapered and comprise all elastomeric material (FIG. 26) or a set of bristles 2818 partially surrounded by elastomeric material 2720, 2820 (FIGS. 27 and 28). The elastomeric material should extend along the length of finger 2616, 2716, 2816 a sufficient distance to facilitate attachment of ribs as described in more detail below.

To facilitate the therapeutic movement of fingers 1716–3116 it is important that head 1714 of toothbrush 1710 be flexible and that fingers 1716–3116 be flexibly mounted in head 1714. FIG. 25 illustrates one form of flexible mounting of fingers in head 2514. In this embodiment the head 2514 has a box-like shape in cross section. At least the upper face 2522 of head 2514, and preferably the entirety of head 2514, is made of a flexible material so that the axes of fingers 2516 can move relative to the plane of toothbrush 1710. The fingers 2516 project from apertures 2526 in the flexible upper face 2522 of head 2514. Any rib and finger 2216, 2316, 2416 arrangement shown in FIGS. 22–24 can be molded into the toothbrush head 2214. This flexible mounting in a flexible portion 2222 of head 2214 assists in obtaining the desired lateral movement of fingers relative to the axes of toothbrush 1710. The role of ribs in obtaining that movement is explained below.

Another means of imparting movement to the fingers 3016, 3116 is illustrated in FIGS. 30 and 31. As illustrated, fingers 3016, 3116 are physically linked to a flexible face 3022A, 3122A of head 3014, 3114 by angled rib 3024, 3124. Rib 3024, 3124 can be integrally molded into head 3014, 3114 and finger 3016, 3116 during the manufacture of toothbrush 1710. It can also be formed of a more rigid (than elastomeric) material such as polypropylene in order to enhance lateral movement of fingers 3016, 3116. Flexible face 3022A, 3122A of head 3014, 3114 in this embodiment can be molded around frame members 3026, 3126 forming the outer periphery of head 3014, 3114. These frame members 3026, 3126 of head 3014, 3114 may be attached to handle 1712 of toothbrush 1710 in a known manner.

The role of ribs 1824–2124 and flexible head 1814–2114 in imparting lateral movement to fingers 1816 is illustrated in FIGS. 18–21. FIG. 18 illustrates the location of fingers 1816 and ribs 1824 (having ends 1828) along outer edges of flexible face 1822 of head 1814. Other groups of bristles or cleaning elements 1817 are arranged inboard of fingers 1816 as illustrated in FIG. 18. Fingers 1816 on the outer edge of head 1614 are closest to the gum line when the user holds the toothbrush in a normal position, i.e., with the longitudinal axis perpendicular to the axis of the user's teeth. Ribs 1824 extend from the side of finger 1816 to the face 1822 of flexible head 1814. These ribs can have a triangular, trapezoidal or like shape that interconnect the finger 1816 to the face of flexible head 1814. This interconnection assures lateral movement of finger 1816 as the face 1822 deflects outward or inward along the longitudinal axis when in use as described below.

The lateral movement of finger 1916–2116 is illustrated in the sequence shown in FIGS. 19–21. In FIG. 19 there is no deflection of face 1922 or rib 1924 of flexible head 1914. FIG. 20 represents a deflection of face 2022 that stretches that face as shown by the arrows 2023 at the edge of this fragmental view. When so stretched the ends 2028, 2128 of rib 2024 anchored to face 2022 move away from each other. That movement exerts a lateral force on finger 2016 causing it to move laterally toward the outside periphery of head 2014 as indicated by the arrow 2025 in FIG. 20. Conversely, when deflection (arrows 2123) of face 2122 of head 2114 causes that face to compress, the ribs 2124 push finger 2116 laterally in the opposite direction as indicated by the arrow 2125 in FIG. 21. Thus, as various forces are transmitted to flexible face 2122 of head 2114 during use, that head moves in compression or expansion. That movement causes fingers 2116 to move in a lateral direction thereby promoting tooth cleaning and gum stimulation.

Another embodiment of the invention illustrated in FIGS. 30 and 31 shows ribs 3024, 3124 oriented approximately 90 degrees to the longitudinal axis of toothbrush 1710 versus approximately 45 degrees shown in FIGS. 18–21. In the former embodiment, movement of the flexible face 3022A in an upward direction (FIG. 30) causes lateral inward movement of fingers 3016 as illustrated by the arrows 3127 in this Figure. Conversely, downward movement of flexible face 3022A would cause lateral movement of fingers 3016 away from each other toward the outside of head 3014 (not illustrated).

Other arrangements of ribs 2224, 2324, 2424 (having ends 2228, 2328, 2428) and their attachment to fingers 2216, 2316, 2416 on faces 2222, 2322, 2422 are illustrated in FIGS. 22–24. As illustrated, multiple fingers 2216, 2316, 2416 are interconnected by a continuous rib 2224, 2324, 2424. FIG. 22 illustrates the interconnecting ribs 2224 on one side of fingers 2216. Thus, upon deflection of flexible face 2222 of head 2214 all fingers 2216 move in the same direction as indicated by the arrows 2229, 2329 in FIGS. 22 and 23. If it were desirable to have the fingers 2416 move in different directions the arrangement of ribs 2424 shown in FIG. 24 can be utilized.

Any suitable form of cleaning elements may be used as the cleaning elements 1817 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions.

It is to be understood that the specific illustration of the cleaning elements is merely for exemplary purposes. The invention can be practiced with various combinations of the same or different cleaning element configurations (such as stapled or in-molded technology bristles, etc.) and/or with the same bristle or cleaning element materials (such as nylon bristles, spiral bristles, rubber bristles, etc.). Similarly, while FIG. 18 illustrates the cleaning elements to be generally perpendicular to head 1814, some or all of the cleaning elements may be angled at various angles with respect to the outer surface of head 1814. It is thereby possible to select the combination of cleaning element configurations, materials and orientations to achieve specific intended results to deliver additional oral health benefits, like enhanced cleaning, tooth polishing, tooth whitening and/or massaging of the gums.

FIG. 29 illustrates a powered toothbrush 2910A containing the fingers 2916 of the invention mounted on a flexible head 2914 of the toothbrush. Cleaning elements 1817 are preferably mounted inboard of fingers 1816 as illustrated in FIG. 18. This embodiment includes a power driven movable disc or section 2930 having cleaning elements (FIG. 29). The movable section 2930 could be oscillated rotationally such as by using the type of drive mechanism shown in U.S. Pat. No. 5,625,916, or could move in and out using the type of drive mechanism shown in U.S. Pat. No. 35,941; all of the details of both patents are incorporated herein by reference thereto. Although FIG. 29 shows movable section 2930 to be at the distal end of the head, the movable section(s) could be located at any desired location on the head.

Referring to FIGS. 32 and 33, an exemplary toothbrush including a head plate according to the invention is illustrated and generally indicated at 3200.

Toothbrush 3200 includes a handle 3202 at a proximal end thereof, and a brush section 3204 that is defined by a neck 3210 that terminates in a head 3220 at a distal end of toothbrush 3200. Handle 3202 has a free proximal end 3208 and an opposite neck end 3206. Neck 3210 generally includes a first end 3214 and a second end 3216 with first end 3214 being located at neck end 3206 of handle 3202 and the second end 3216 being located at head 3220. In other words, neck 3210 is the portion of toothbrush 3200 that extends between handle 3202 and head 3220. Head 3220 is preferably generally aligned with the longitudinal axis x—x of toothbrush 3200.

Neck 3210 and handle 3202 may be constructed as a unitary member by forming neck 3210 integral to handle 3202 at neck end 3206 of handle 3202, or may be formed detachable from handle 3202 at the neck end 3206. In accordance with this detachable embodiment, the combined neck 3210 and head 3220 can be removed from handle 3202 to permit cleaning, servicing and/or interchanging of either handle 3202 or the combined neck 3210 and head 3220 (brush section 3204). When neck 3210 is formed to be detachable from handle 3202, first neck end 3214 preferably includes a connector linkage (not shown) that is adapted to be detachably joined to handle 3202 using traditional techniques. It will also be appreciated that the point of detachment may be between head 3220 and neck 3210 such that head 3220 is of a refill head type.

It will further be appreciated that the illustrated shapes of handle 3202 and neck 3210 are merely exemplary in nature and handle 3202 and/or neck 3210 can be formed to have any number of shapes. Preferably, the shapes of handle 3202 and neck 3210 are ergonomically pleasing to a user of toothbrush 3200 and provide a toothbrush that is easily gripped and held and easily manipulated by a user. For example, handle 3202 may include a slightly recessed finger section 3218 which is formed on handle 3202. The recessed finger section 3218 is designed to receive the thumb of one hand to thereby assist a user in proper placement of toothbrush 3200 in a user's hand. Recessed finger section 3218 may include ribs or another type of roughened surface to assist a user in gripping toothbrush 3200 at recessed finger sections 3218. Of course other patterns for providing recessed finger sections may be employed.

The head plate for the bristles is formed with a solid perimeter and defines a field of variously shaped and sized holes within this perimeter. Fibers that are to form the tufts are then placed in the holes in the field of the head plate, and the backs of the tufts are melted together to fix their position relative to one another.

The tufted head plate is then inserted into a predefined receiving portion of the head portion of a toothbrush handle and is sonically welded into place. The brush is then end rounded and packaged for sale as a traditional toothbrush.

As is shown in FIGS. 32 and 33 of the present invention, a head plate 3250 is provided, and is fixed to head 3220 of toothbrush 3200, preferably by sonic welding, although any other appropriate attachment technique may be employed. Head plate 3250 is formed of at least two materials. A first rigid material is used to form the perimeter portion 3252 of the head plate. Such a material, such as for example polypropylene, is easily sonically welded. A tuft field 3254 is formed of a flexible elastomer (preferably having a hardness of 90 Shore A or less).

A process known as "Anchor Free Tufting" (AFT) is used in the formation of head 3250. In such an AFT process, head plate 3250 is used for holding toothbrush bristles in their proper orientation. When the bristles are placed in their proper orientation through the corresponding holes in the head plate 3250, the head plate 3250 is placed in the head plate cavity formed in the front face of the head section 3204 of the brush, and for insertion into a toothbrush.

As is best shown in FIG. 32, head plate 3250 is formed with a solid perimeter and defines a field of variously shaped and sized apertures or holes 3256 within the flexible elastomer tuft field 3254. Fibers that are to form one or more bristle tufts 3258 are then placed in the holes in field 3254 of head plate 3250, and the backs of tufts 3258 are melted together to fix their position relative to one another. Thus, such a head plate is able to flex, thereby allowing the tuft field and bristles to move under normal brushing conditions, while providing a perimeter of structural rigidity that is able to be sonically welded. Therefore, the head plate and bristles move or flex under the pressure of normal brushing. While bristles 3258 are shown, elastomeric members may also be used in place of these tufts. Furthermore, while a particular tuft field pattern is shown, any desirable tuft field pattern may be employed. Furthermore, the bristle material need not be the same for all of the tufts, and indeed varying materials for performance color or indication of life remaining in the brush head, may be used exclusively, or in combination as desired.

The toothbrush according to the various embodiments disclosed herein can be made from any number of materials that are suitable for use in oral care products, such as toothbrushes, etc. For example, many of the components that are included in toothbrush are formed of plastic materials.

Accordingly, the handle and head of the powered toothbrush may be molded from polyolefins such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyamide 6), polyesters (for example polyester ester or polyether ester), polyurethanes (for, example polyesterurethane, polyetherurethane or polyesteretherurethane).

Various modifications and variations of the described compositions, materials and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art or in related fields are intended to be within the scope of the following claims.

What is claimed is:

1. A toothbrush comprising:
a handle;
a neck connected to said handle;
a head connected to said neck and having a rigid portion having a first surface and a second surface, and a movable portion having a first surface and a second surface, wherein said rigid portion is non-movable relative to said neck and wherein said movable portion is movable relative to said neck;
a mechanical vibratory device which causes the head to vibrate;
wherein said rigid portion comprises a plurality of first cleaning elements extending from said first surface of said rigid portion that are fixedly mounted to the rigid portion, said rigid portion being an upstanding wall that creates a peripheral frame having a central opening;
wherein said movable portion comprises a plurality of second cleaning elements extending from said first surface of said movable portion that are fixedly mounted to said movable portion, said movable portion located within the central opening;
an annular gap in the head positioned between said rigid portion and said movable portion;
a resilient membrane for flexibly attaching said movable portion to said rigid portion, said membrane positioned in a part of said gap; and
a plurality of third cleaning elements, each third cleaning element mounted on said resilient membrane and connected to both said rigid portion and said movable portion; wherein no portion of any of the third cleaning elements extends outwardly beyond the second surfaces of said movable and rigid portions under any condition.

2. The toothbrush according to claim 1, wherein the plurality of third cleaning elements comprise movable wipers generally arrayed in surrounding relation to said plurality of second cleaning elements.

3. The toothbrush according to claim 2, wherein the movable wipers rotate towards one another upon application of sufficient force on the toothbrush and away from each other upon release of that force.

4. The toothbrush according to claim 1, wherein said mechanical vibratory device is located in the head or in a region adjacent to the head and operatively connected to an electric power source.

5. The toothbrush according to claim 1, wherein the first, second and third cleaning elements extend approximately the same distance from the head when no force is applied to said toothbrush.

6. The toothbrush according to claim 1, wherein at least one of said plurality of third cleaning elements is movable toward at least one of said first and second cleaning elements.

7. The toothbrush according to claim 1, wherein at least one of said plurality of third cleaning elements is movable toward each of said first and second cleaning elements.

8. The toothbrush according to claim 1 wherein the first surface of the movable portion remains aligned with or below a plane defined by the first surface of the rigid portion under any condition.

9. The toothbrush according to claim 1 wherein said resilient membrane is made of an elastomeric material capable of flexing and recovering randomly during use of the toothbrush.

10. A toothbrush comprising:
a handle;
a head connected to the handle and having a front side and a rear side, the head comprising:
an upstanding wall that forms a peripheral frame that circumferentially surrounds a central opening;
a platform positioned within the central opening so that the platform is separated from the upstanding wall by an annular gap; and
a resilient material positioned in at least a portion of the annular gap that flexibly attaches the platform to the upstanding wall;
a first group of cleaning elements fixedly mounted to and extending from said upstanding wall;
a second group of cleaning elements fixedly mounted to and extending from said platform, the first and second groups of cleaning elements extending outward from the front side of the head;
wherein upon a user contacting one or more teeth with the first and second groups of cleaning elements and applying pressure, the resilient material flexes and the platform moves toward the rear side of the head, allowing the first group of cleaning elements to contact areas of the teeth located further from the head; and
a third group of cleaning elements mounted on the resilient material and extending outward from the front side of the head, the third group of cleaning elements arranged on opposing sides of the platform so that as the platform moves toward the rear side of the head, the third group of cleaning elements rotate inward toward the second group of cleaning elements.

11. The toothbrush of claim 10 wherein the resilient material that flexibly attaches the platform to the upstanding wail is a flexible elastomeric material.

12. The toothbrush of claim 10 wherein the resilient material that flexibly attaches the platform to the upstanding wall is in a form selected from a group consisting of a membrane, plastic straps, webbing, and a plurality of spaced-apart bridges.

13. The toothbrush of claim 10 wherein the handle further comprises a neck, the upstanding wall being non-movable with respect to the neck.

14. The toothbrush of claim 10 wherein the first group of cleaning elements circumferentially surround the central opening.

15. The toothbrush of claim 10 wherein the resilient material is an elastomeric material and the third group of cleaning elements are elastomeric wipers, the elastomeric wipers integrally formed with the elastomer material that flexibly attaches the platform to the upstanding wall.

16. The toothbrush of claim 10 further comprising a mechanical vibratory device which causes the head to vibrate.

17. The toothbrush of claim 10 wherein the first and second groups of cleaning elements are bristles and the third group of cleaning elements are elastomeric wipers.

18. The toothbrush of claim 10 wherein the first and second groups of cleaning elements are bristles and the third group of cleaning elements are elastomeric wipers;
    wherein the resilient material are flexibly attaches the platform to the upstanding wall is in a form selected from a group consisting of a membrane, plastic straps, webbing, and a plurality of spaced-apart bridges;
    wherein the handle further comprises a neck, the upstanding wall being non-movable with respect to the neck: and
    wherein the first group of cleaning element circumferentially surround the central opening.

* * * * *